(12) United States Patent
Hartridge et al.

(10) Patent No.: US 11,787,680 B2
(45) Date of Patent: Oct. 17, 2023

(54) FLUID DISTRIBUTION SYSTEM WITH SINGLE USE MANIFOLD FLUID RECOVERY ASSEMBLY

(71) Applicant: Cytiva US LLC, Marlborough, MA (US)

(72) Inventors: Thomas J. Hartridge, Hampshire (GB); Bojan Isailovic, Hampshire (GB); Jens Bretschneider, Dreieich (DE)

(73) Assignee: Cytiva US LLC, Marlborough, MA (US)

( * ) Notice: Subject to any disclaimer, the term of this patent is extended or adjusted under 35 U.S.C. 154(b) by 0 days.

(21) Appl. No.: 17/934,486

(22) Filed: Sep. 22, 2022

(65) Prior Publication Data

US 2023/0211994 A1    Jul. 6, 2023

Related U.S. Application Data

(60) Provisional application No. 63/295,490, filed on Dec. 30, 2021.

(51) Int. Cl.
*B67C 3/22* (2006.01)
*B65B 3/00* (2006.01)
(Continued)

(52) U.S. Cl.
CPC .............. *B67C 3/225* (2013.01); *B65B 3/003* (2013.01); *B65B 3/12* (2013.01); *B65B 55/24* (2013.01);
(Continued)

(58) Field of Classification Search
CPC ........... B65B 3/003; B65B 3/12; B65B 55/24; B67C 3/225; B67C 3/007; B67C 3/282; B67C 2003/228
See application file for complete search history.

(56) References Cited

U.S. PATENT DOCUMENTS 5,911,252 A * 6/1999 Cassel ..................... B65B 3/003
604/407
6,712,963 B2 * 3/2004 Schick ................ A61M 1/0218
210/257.2
(Continued)

FOREIGN PATENT DOCUMENTS

EP         3845628 A1     7/2021

OTHER PUBLICATIONS

European Patent Office, Extended European Search Report in European Patent Application No. 22216942.7 (dated Jul. 7, 2023).

*Primary Examiner* — Nicolas A Arnett
(74) *Attorney, Agent, or Firm* — Leydig, Voit & Mayer, Ltd.

(57) ABSTRACT

A fluid distribution system includes single use distributor manifolds each having a distributor manifold inlet and a plurality of distributor manifold outlets in fluid communication with the distributor manifold inlet. A set of single use filler manifolds can be sequentially connected to a respective one of the outlets of a single use distributor manifold immediately upstream of the connection point of the set of single use filler manifolds. In embodiments, an upstream distributor manifold can be used to feed fluid to a set of intermediary distributor manifolds where the set of intermediary distributor manifolds corresponds to the number of outlets of the upstream distributor manifold.

20 Claims, 21 Drawing Sheets

(51) Int. Cl.
*B65B 3/12* (2006.01)
*B65B 55/24* (2006.01)
*B67C 3/00* (2006.01)
*B67C 3/28* (2006.01)

(52) U.S. Cl.
CPC .............. *B67C 3/007* (2013.01); *B67C 3/282* (2013.01); *B67C 2003/228* (2013.01)

(56) References Cited

U.S. PATENT DOCUMENTS

| | | | |
|---|---|---|---|
| 7,343,943 B2* | 3/2008 | Khan | B65B 3/003 |
| | | | 141/2 |
| 10,549,248 B2* | 2/2020 | Brown | A61M 39/223 |
| 10,954,007 B2* | 3/2021 | Feith | A61J 3/002 |
| 11,319,201 B2* | 5/2022 | Zumbrum | B67C 3/225 |
| 11,648,182 B2* | 5/2023 | Oda | A61J 3/002 |
| | | | 141/27 |
| 2016/0368629 A1 | 12/2016 | Storey | |
| 2017/0361966 A1* | 12/2017 | Havel | B65B 39/00 |
| 2021/0155507 A1* | 5/2021 | Kamen | C02F 1/441 |
| 2021/0197142 A1* | 7/2021 | Seal | B01F 23/49 |
| 2021/0325212 A1* | 10/2021 | Lamport | B01F 25/4316 |
| 2022/0380069 A1* | 12/2022 | Cataldo | B65B 59/04 |

* cited by examiner

FLUID DISTRIBUTION SYSTEM WITH SINGLE USE MANIFOLD FLUID RECOVERY ASSEMBLY

CROSS-REFERENCE TO RELATED APPLICATIONS

This patent application claims the benefit of priority to U.S. Provisional Patent Application No. 63/295,490, filed Dec. 30, 2021, and entitled, "Fluid Distribution System with Single Use Manifold Fluid Recovery Assembly," which is incorporated in its entirety herein by this reference.

BACKGROUND OF THE INVENTION

The use of a single-use system (SUS), such as, for example, biocontainer bags and the like, is becoming more widespread for biopharmaceutical applications. An SUS can be used in systems such as, bioreactors and mixing systems. Exemplary upstream SUS applications include media preparation processes such as mixing and filtration, including tangential flow filtration (TFF), for example. Examples of downstream SUS applications include chromatography concentration and diafiltration and buffer preparation, for example.

The adoption of an SUS can offer several advantages over conventional reusable stainless steel systems. Single-use technology can increase process flexibility and reduce cross contamination risks; reduce or even eliminate the need for cleaning; reduce requirements for in-house sterilization, such as by autoclaving, and cleaning chemical inventory; and lower process downtime.

An aspect of biopharmaceutical processing involves managing the movement of liquid through a myriad of elements including tubing, valves and sensors. There is a requirement particularly with a bulk filling process to aliquot fluids from a large container to multiple individual containers while maintaining sterility.

In conventional systems, fluid can remain in the manifold of the fluid distribution system after a filling sequence has been performed. For typical drug fluid, the cost of every milliliter of product can be several thousand dollars. In some instances, an operator may manually manipulate the manifold to force fluid from the manifolds into an "odd" container for each change over. These containers will be "odd" because they will not contain the exact volume as in the customer fill containers, and, therefore, the fluid in them is often discarded, used for off-line analytics, or otherwise not included in the final drug formulation. This is not only a costly loss but also reduces the amount of drug produced in the final formulation and decreases the number of drug doses per batch for patient treatments.

There is a continued need in the art for single use applications related to the distribution of fluid from a supply to a number of smaller containers. For example, there is a continued need in the art to provide additional solutions for aliquoting liquid in a sterile manner to a substantial number of outlets, and hence containers such as bags and bottles, while reducing the amount of fluid that is wasted during the filling operations.

It will be appreciated that this background description has been created to aid the reader, and is not to be taken as an indication that any of the indicated problems were themselves appreciated in the art. While the described principles can, in some aspects and embodiments, alleviate the problems inherent in other systems, it will be appreciated that the scope of the protected innovation is defined by the attached claims, and not by the ability of any disclosed feature to solve any specific problem noted herein.

BRIEF SUMMARY OF THE INVENTION

The present disclosure, in one aspect, is directed to embodiments of a fluid distribution system. In one embodiment, a fluid distribution system includes a pump, a single use filler manifold, a filler valve arrangement, and a control unit.

The pump is adapted to selectively produce a flow of fluid. The single use filler manifold includes a filler manifold inlet, a plurality of filler manifold outlets, and a filler manifold body conduit. The filler manifold inlet is in fluid communication with each one of the plurality of filler manifold outlets via the filler manifold body conduit. The filler manifold inlet is arranged with the pump for delivering a supply of fluid to the single use filler manifold. The filler manifold outlets comprise at least one standard fill outlet and an underfill outlet. The filler valve arrangement includes a plurality of valves arranged with the single use filler manifold such that each of the filler manifold outlets is independently occludable via a respective one of the valves of the filler valve arrangement.

The control unit includes a processor and a non-transitory computer readable medium bearing a fluid distribution program. The processor is arranged with the computer readable medium to execute the fluid distribution program. The processor is in electrical communication with the pump and the filler valve arrangement to selectively operate the pump and the valves of the filler valve arrangement based upon instructions from the fluid distribution program. The fluid distribution program has a container filling module configured to discharge a target fill volume of the supply of fluid out of each standard fill outlet of the filler manifold outlets, discharge an underfill volume of the supply of fluid out of the underfill outlet of the filler manifold outlets, and drain a filler manifold volume of the supply of fluid from the filler manifold body conduit out of the underfill outlet of the filler manifold outlets. The underfill volume is less than the target fill volume.

In another aspect, the present disclosure is directed to embodiments of techniques of aseptically distributing fluid. In one embodiment, a method of aseptically distributing fluid includes feeding a supply of fluid into a filler manifold inlet of a single use filler manifold. A fill portion of the supply of the fluid is discharged respectively from all but a reserved one of a plurality of filler manifold outlets of the first single use filler manifold to single use containers respectively aseptically fluidly connected thereto. After fill portion discharging, an underfill portion of the supply of the fluid is discharged from the reserved one of the filler manifold outlets to a single use container aseptically fluidly connected thereto. The underfill portion is less than the fill portion. After underfill portion discharging, a filler manifold volume of the supply of fluid is drained from a body conduit of the single use filler manifold out of the reserved one of the filler manifold outlets to the single use container aseptically fluidly connected thereto.

Further and alternative aspects and features of the disclosed principles will be appreciated from the following detailed description and the accompanying drawings. As will be appreciated, the fluid distribution systems and the methods of aseptically distributing fluid disclosed herein are capable of being carried out in other and different embodiments, and capable of being modified in various respects. Accordingly, it is to be understood that both the foregoing

Figure 1:
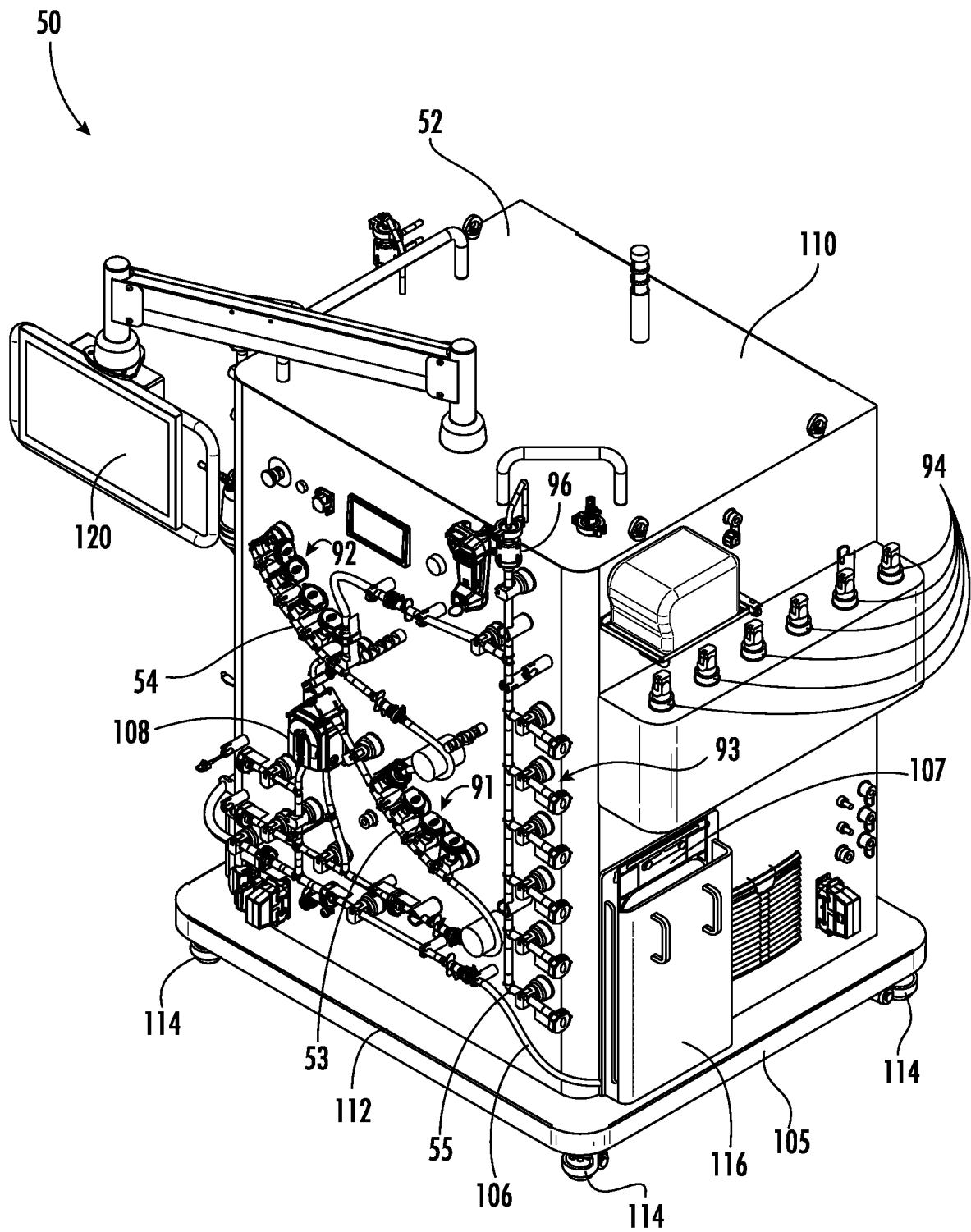
FIG. 1 is a perspective view of an embodiment of a fluid distribution system constructed in accordance with principles of the present disclosure in the form of an embodiment of a distributor skid constructed in accordance with principles of the present disclosure.

It should be understood that the drawings are not necessarily to scale and that the disclosed embodiments are illustrated diagrammatically and in partial views. In certain instances, details which are not necessary for an understanding of this disclosure or which render other details difficult to perceive may have been omitted. It should be understood that this disclosure is not limited to the particular embodiments illustrated herein.

DETAILED DESCRIPTION OF THE INVENTION

Embodiments of a fluid distribution system constructed in accordance with principles of the present disclosure are adapted to be used with embodiments of a method of aseptically distributing fluid following principles of the present disclosure. Embodiments of a fluid distribution system constructed in accordance with principles of the present disclosure can be used in biopharmaceutical environments, and can be used in other industrial applications where different fluids, solutions, reagents and/or chemicals are stored for metering to a process station.

For example, embodiments of a fluid distribution system constructed in accordance with principles of the present disclosure are adapted to be used in a bioprocessing system in which a supply of fluid is distributed to a plurality of containers for use in a bioprocessing application. Embodiments of a fluid distribution system constructed in accordance with principles of the present disclosure can be used to perform applications related to bulk filling in pharmaceutical drug production. Embodiments of a fluid distribution system constructed in accordance with principles of the present disclosure can be used to perform applications related to formulating, filling, and other applications related to aliquoting liquids in a sterile manner.

In embodiments, the fluid distribution system includes a scalable series of single use manifolds in serial fluid communication with each other in a closed, sterile system. In embodiments, the fluid distribution system includes two, three, or more single use manifolds fluidly connected together in series to effectively increase the number of containers that can be filled in a sterile manner via the foremost upstream single use manifold to a number greater than the number of outlets present therein. The number of containers that can be filled using a fluid distribution system constructed according to principles of the present disclosure is therefore scalable to satisfy the particular parameters of a given application.

In embodiments, the fluid distribution system includes a single use distributor manifold adapted for sequential aseptic fluid connection with a set of single use filler manifolds corresponding to the number of distributor manifold outlets. In embodiments, each manifold comprises a replaceable part that is installed in the fluid distribution system for single use in a bioprocessing application and uninstalled after its intended single use for disposal thereof. In embodiments, the fluid distribution system includes an upstream single use distributor manifold adapted for sequential aseptic fluid connection with a set of intermediary single use distributor manifolds corresponding to the number of distributor manifold outlets of the upstream single use distributor manifold. The system also includes multiple sets of single use filler manifolds in which each respective set corresponds to the number of distributor manifold outlets of a respective one of the set of intermediary distributor manifolds.

In embodiments, the fluid distribution system is incorporated into a distributor skid including at least one single use distributor manifold and a set of single use filler manifolds adapted to be placed in fluid communication with one of a plurality of distributor manifold outlets. In yet other embodiments, the fluid distribution system is incorporated into a distributor skid and one or more distribution towers in which the distribution tower is adapted to receive one of a set of single use filler manifolds.

Embodiments of a fluid distribution system constructed in accordance with principles of the present disclosure are configured as a relatively compact solution to achieve a scalable range of different fluid distributing solutions for an intended use in a bioprocessing application. Embodiments of a fluid distribution system constructed in accordance with principles of the present disclosure can include a supply of fluid, at least one single use distributor manifold, a set of single use filler manifolds each having a filler manifold inlet adapted to be placed in fluid communication with one of a plurality of distributor manifold outlets and a plurality of filler manifold outlets, and multiple containers corresponding to the product of the number of filler manifold outlets and the number of single use filler manifolds in the set. Multiple sets of containers can be respectively filled with each of the set of single use filler manifolds in a relatively small footprint (particularly relative to a conventional distribution tower configured for use in a similar bioprocessing application) for storing therein fluid for use in a predetermined bioprocessing application. The containers can be delivered to a storage area (such as, for example, a workstation supporting a plurality of biocontainer bags for use in a bioprocessing application (such as, for example, a chromatography/tangential flow filtration (TFF) application, for example) on demand. Embodiments of a fluid distribution system constructed in accordance with principles of the present disclosure can be used as a replacement for conventional systems for a comparable bioprocessing application that use one single use manifold at a time for filling no more containers than the number of outlets of the single use manifold.

Embodiments of a fluid distribution system constructed in accordance with principles of the present disclosure are configured to drain the fluid volume from the body of the single use filler manifold into a reserved fill container of a set of fill containers and so form part of the "usable" customer product fluid. Embodiments of a fluid distribution system constructed in accordance with principles of the present disclosure are configured to perform a specific automated method in which after each manifold changeover, the fluid from the above-mentioned multiplier manifolds is fully recovered into a recovery bag and reintroduced into the system to fill and prime the newly installed manifolds. Accordingly, after the batch completion (as per the case scenario described above), there will be only one "odd" volume in the recovery bag (rather than after each separate fill sequence as in conventional techniques).

Embodiments of a fluid distribution system constructed in accordance with principles of the present disclosure include a control unit programmed with a fluid distribution program having a container filling module configured to discharge a target fill volume of the supply of fluid out of each standard fill outlet of the filler manifold outlets, discharge an underfill volume of the supply of fluid out of the underfill outlet of the filler manifold outlets, and drain a filler manifold volume of the supply of fluid from the filler manifold body conduit out of the underfill outlet of the filler manifold outlets. The underfill volume is less than the target fill volume.

In bulk product dispensing applications, the entrapment of air in both the flow path as well as in the final fill containers risks negatively affecting the process. Air in the flow path can reduce the system's ability to dispense fluid accurately, thereby increasing dispensing variability and adversely affecting the formulation process downstream. Air in the final containers may reduce the product quality as some products may be sensitive to oxygen and/or reduce the efficiency of the process of freezing fluid in these containers. Embodiments of a fluid distribution system constructed in accordance with principles of the present disclosure include a control unit programmed with a fluid distribution program to automatically remove air trapped within the manifolds to enhance the accuracy and consistency of the fluid dispensing process.

Figure 2:
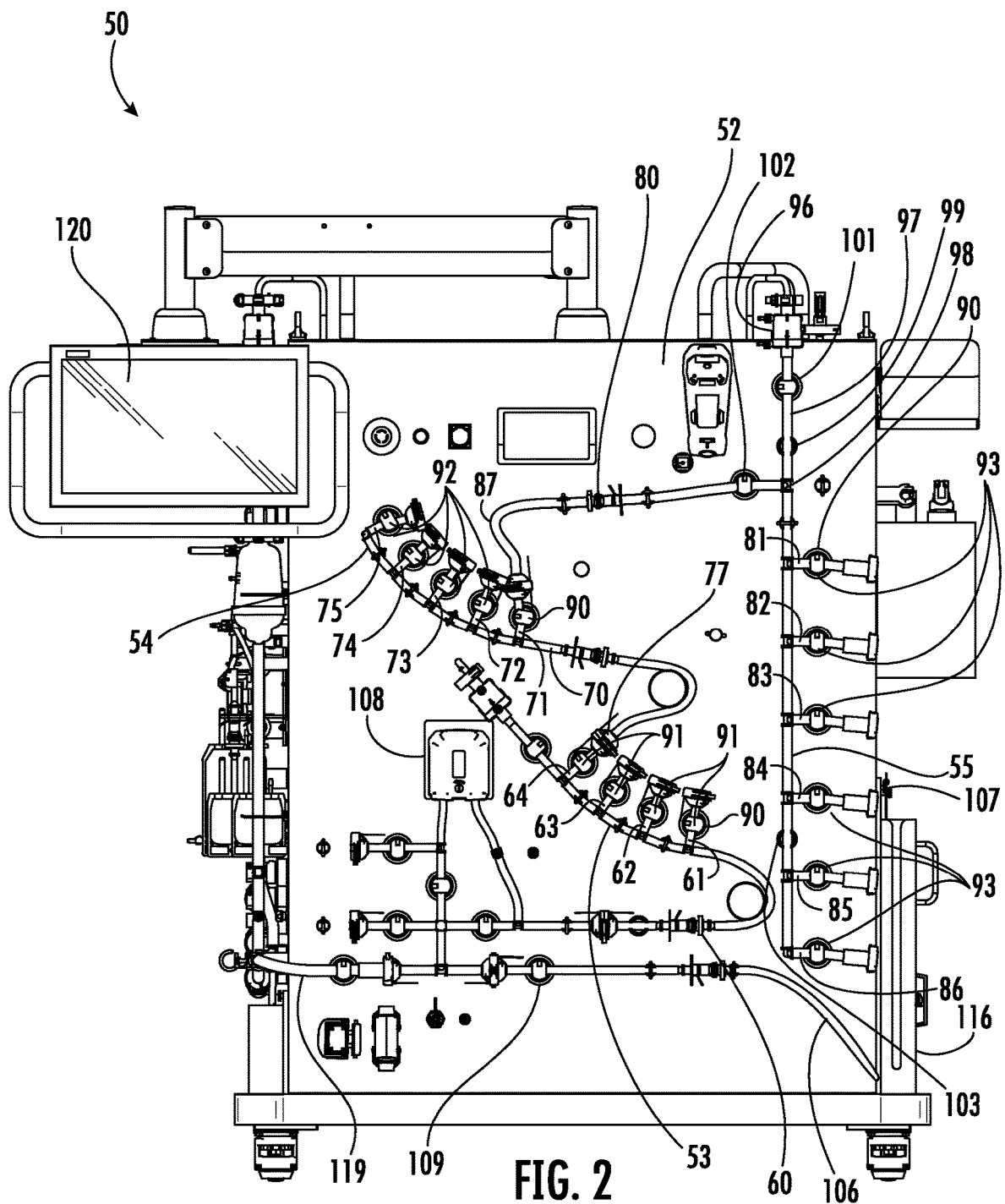
FIG. 2 is an elevational view of the distributor skid of FIG. 1.

Turning now to the FIGURES, there is shown in FIGS. 1 and 2 an embodiment of a fluid distribution system 50 constructed in accordance with principles of the present disclosure that is incorporated into a distributor skid 52 constructed in accordance with principles of the present disclosure that includes an upstream single use distributor manifold 53, an intermediary single use distributor manifold 54, and a single use filler manifold 55 fluidly connected together in series. The distributor skid 52 includes a pump 57 (see FIG. 3) configured to draw fluid from a supply of fluid (not shown) and deliver it to the manifolds 53-55 which are connected in series.

In the illustrated embodiment, each manifold 53-55 comprises a replaceable part that is installed once in the distributor skid 52 for use in a bioprocessing application and uninstalled thereafter for disposal thereof. After completing its intended use in the bioprocessing application, the respective manifold 53-55 can be disconnected from the distributor skid 52 according to a predetermined hierarchy and replaced with another single use manifold having a similar construction.

In embodiments, the fluid distribution system 50 can be used with any suitable fluid, which can be stored in a suitable container, such as a tote, for example, which is in fluid communication with the pump 57. In embodiments, a fluid distribution system 50 constructed in accordance with principles of the present disclosure can include at least two single use manifolds fluidly 54, 55 connected together in series.

The intermediary single use distributor manifold 54 is one of a set of intermediary single use distributor manifolds 54 that have substantially the same construction and are configured to be sequentially mounted to the distributor skid 52. Similarly, the single use filler manifold 55 is one of a set of single use filler manifolds 55 that have substantially the same construction are configured to be sequentially mounted to the distributor skid 52. The illustrated fluid distribution system 50 is configured to receive fluid (such as, buffer solutions for use in an intended bioprocessing application, e.g., chromatography, TFF, etc.) from a supply and serially distribute the fluid to as many as one hundred twenty containers sequentially using the sets of single use filler manifolds 55 and single use distributor manifolds 54 before replacing the upstream single use distributor manifold 53 and opening the closed system (six outlets for each one of the set of twenty single use filler manifolds 55×five outlets for each one of the set of four intermediary single use distributor manifolds 54×four outlets of the upstream single use distributor manifold 53).

In other embodiments, the fluid distribution system 50 can be configured to fill a different maximum number of containers in a closed system before it would need to be opened to continue distributing fluid to more containers. In embodiments, the set of intermediary single use distributor manifolds 54 can include at least one manifold having a construction different from at least one other manifold of the set (e.g., a different number of outlets), and, in embodiments, the set of single use filler manifolds 55 can include at least one manifold having a construction different from at least one other manifold of the set (e.g., a different number of outlets).

Referring to FIG. 2, each of the upstream single use distributor manifold 53, the intermediary single use distributor manifold 54, and the single use filler manifold 55 can have a similar construction. In the illustrated embodiment, each manifold 53-55 includes a tubing arrangement that interconnects the various ports of the manifold and is associated with control valves to control the flow of fluid through the manifold. In embodiments, the tubing arrangement comprises a plurality of flexible tubing lines adapted to be selectively occluded by a pinch valve externally mounted thereto. In embodiments, the flexible tubing can be made from any suitable material, such as, silicone, thermoplastic elastomer (TPE), etc.

In embodiments, the manifolds 53-55 can be made from any suitable material and can comprise suitable tubing defining fluid conduits therethrough. In embodiments, the manifolds 53-55 comprise any one of a range of suitable materials and assemblies as will be readily known to one of ordinary skill in the art, such as, e.g., silicone tubing, plastic injection molded adapters, and commercially-available connectors and disconnectors (e.g., Kleenpack® Presto sterile connectors and Kleenpack® sterile disconnectors from Pall Corporation of New York). The illustrated manifolds 53-55 are made from tubing that can be selectively occluded by a pinch valve.

The upstream single use distributor manifold 53 is removably mounted to the distributor skid 52. The upstream single use distributor manifold 53 has an upstream distributor manifold inlet 60 and a plurality of upstream distributor manifold outlets 61, 62, 63, 64 in fluid communication with the upstream distributor manifold inlet via the hollow body conduit of the manifold 53. The illustrated upstream single use distributor manifold 53 includes four upstream distributor manifold outlets 61-64. In other embodiments, the number of upstream distributor manifold outlets 61-64 can be different. The upstream distributor manifold inlet 60 is fluidly arranged, via suitable tubing and connectors, with the pump 57 mounted to the distributor skid 52 for delivering the supply of fluid to the series of manifolds 53-55.

The intermediary single use distributor manifold 54 is removably mounted to the distributor skid 52. The intermediary single use distributor manifold 54 has an intermediary distributor manifold inlet 70 and a plurality of intermediary distributor manifold outlets 71, 72, 73, 74, 75 in fluid communication with the intermediary distributor manifold inlet 70 via the hollow body conduit of the manifold 54. The intermediary distributor manifold inlet 70 is in fluid communication with one of the upstream distributor manifold outlets, in this case the fourth distributor manifold outlet 64. The illustrated intermediary single use distributor manifold 54 includes five intermediary distributor manifold outlets 71-75. In other embodiments, the number of intermediary distributor manifold outlets 71-75 can be different.

The intermediary single use distributor manifold 54 is one of a set of intermediary single use distributor manifolds 54. The set of intermediary single use distributor manifold 54 corresponds to the number of upstream distributor manifold outlets 61-64, in this case four. Each intermediary single use distributor manifold 54 has an aseptic fluid connector 77 configured to fluidly connect the intermediary distributor manifold inlet 70 to one of the upstream distributor manifold outlets. In embodiments, each intermediary single use distributor manifold 54 of the set of intermediary single use distributor manifolds 54 has a similar construction. In embodiments, at least one intermediary single use distributor manifold 54 of the set of intermediary single use distributor manifolds 54 can have a different construction from at least one other of the set, such as a different number of intermediary distributor manifold outlets from at least one other of the set of intermediary single use distributor manifolds 54.

In embodiments, the distribution manifolds 53, 54 are curved, which allows all connecting tube lengths to be substantially similar. This construction can keep both the manifold length and footprint relatively compact while simplifying the manifold manufacturing process.

The single use filler manifold 55 is removably mounted to the distributor skid 52. The single use filler manifold 55 has a filler manifold inlet 80 and a plurality of filler manifold outlets 81, 82, 83, 84, 85, 86 in fluid communication with the filler manifold inlet 80 via the hollow body conduit of the manifold 55. The filler manifold inlet 80 is in fluid communication with one of the intermediary distributor manifold outlets 71-75, in this case the first intermediary distributor manifold outlet 71. The illustrated single use filler manifold 55 includes six filler manifold outlets 81-86. In other embodiments, the number of filler manifold outlets 81-86 can be different.

In embodiments, the filler manifold outlets 81-86 comprise at least one standard fill outlet and an underfill outlet for use with a container filling module of a fluid distribution program for conserving fluid. In the illustrated embodiment, the single use filler manifold 55 includes five standard fill outlets 81-85 and the bottommost outlet comprises the underfill outlet 86. The container filling module can be configured to discharge a target fill volume of the supply of fluid out of each standard fill outlet 81-85 of the filler manifold outlets 81-86, discharge an underfill volume of the supply of fluid out of the underfill outlet 86 of the filler manifold outlets 81-86, and drain a filler manifold volume of the supply of fluid from the filler manifold body conduit of the single use filler manifold 55 out of the underfill outlet 86 of the filler manifold outlets 81-86. The underfill volume is less than the target fill volume. In embodiments, the underfill volume combined with the filler manifold volume is substantially the same as the target fill volume.

The single use filler manifold 55 is one of a set of single use filler manifolds 55. In embodiments, the set of single use filler manifolds 55 corresponds to the product of the number of outlets for each distributor manifold of two or more distributor manifolds connected in series upstream of the filler manifold inlet. In embodiments where only one single use distributor manifold is in series connection with the filler manifold inlet, the set of single use filler manifolds 55 can correspond to the number of distributor manifold outlets of the single distributor manifold. In the illustrated embodiment, the set of single use filler manifolds 55 includes twenty single use filler manifolds 55, which corresponds to the product of the number of intermediary distributor manifold outlets (five) and the number of upstream distributor manifold outlets (four). In embodiments, the set of single use filler manifolds 55 corresponds to at least the number of intermediary distributor manifold outlets. Each single use filler manifold has an aseptic fluid connector 87 configured to fluidly connect the filler manifold inlet 80 to one of the plurality of intermediary distributor manifold outlets 71-75.

In embodiments, each single use filler manifold 55 of the set of single use filler manifolds 55 has a similar construction. In embodiments, at least one single use filler manifold 55 of the set of single use filler manifolds 55 can have a different construction from at least one other of the set, such as a different number of filler manifold outlets from at least one other of the set of single use filler manifolds 55.

Referring to FIG. 2, the illustrated fluid distribution system 50 includes a valve 90 associated with each outlet of the manifolds 53-55 (only the first of which is marked in FIG. 2). An upstream distributor valve arrangement 91 includes a plurality of valves 90 mounted to the skid 52 and arranged with the upstream single use distributor manifold 53 such that each of the upstream distributor manifold outlets 61-64 is independently occludable via a respective one of the valves 90 of the upstream distributor valve arrangement 91. An intermediary distributor valve arrangement 92 includes a plurality of valves 90 mounted to the skid 52 and arranged with the intermediary single use distributor manifold 54 such that each of the intermediary distributor manifold outlets 71-75 is independently occludable via a respective one of the valves 90 of the intermediary distributor valve arrangement 92. A filler valve arrangement 93 includes a plurality of valves 90 mounted to the skid 52 and arranged with the single use filler manifold 55 such that each of the filler manifold outlets 81-86 is independently occludable via a respective one of the valves 90 of the filler valve arrangement 93.

In embodiments, the valve arrangements 91-93 can comprise any suitable valve adapted to selectively occlude the outlet with which it is associated. In the illustrated embodiment, the valve arrangements 91-93 include pinch valves adapted to control the flow of fluid within the system by occluding the tubing of the manifold to effectively occlude the manifold outlet with which it is associated. The valves 90 are secured to the skid 52 and provide the means for removable mounting the manifolds 53-55 to the skid 52. In other embodiments, a different type of valve can be used, as will be readily familiar to one skilled in the art, such as a solenoid valve, for example. In embodiments, the valves 90 can be operated by a suitable source, such as, a pneumatic source or an electrical power source, for example. In embodiments, the operation of the valves 90 of the valve arrangements 91-93 can be coordinated using a control unit which is suitably programmed to operate one or more desired fluid distributing sequences.

Referring to FIG. 1, the illustrated distributor skid 52 includes a first filler valve arrangement 93 and a second filler valve arrangement 94. The first filler valve arrangement 93 is disposed on a side of the distributor skid 52 including the upstream and intermediary distributor manifolds 53, 54. The second filler valve arrangement 94 is disposed on another side of the distributor skid 52.

Figure 3:
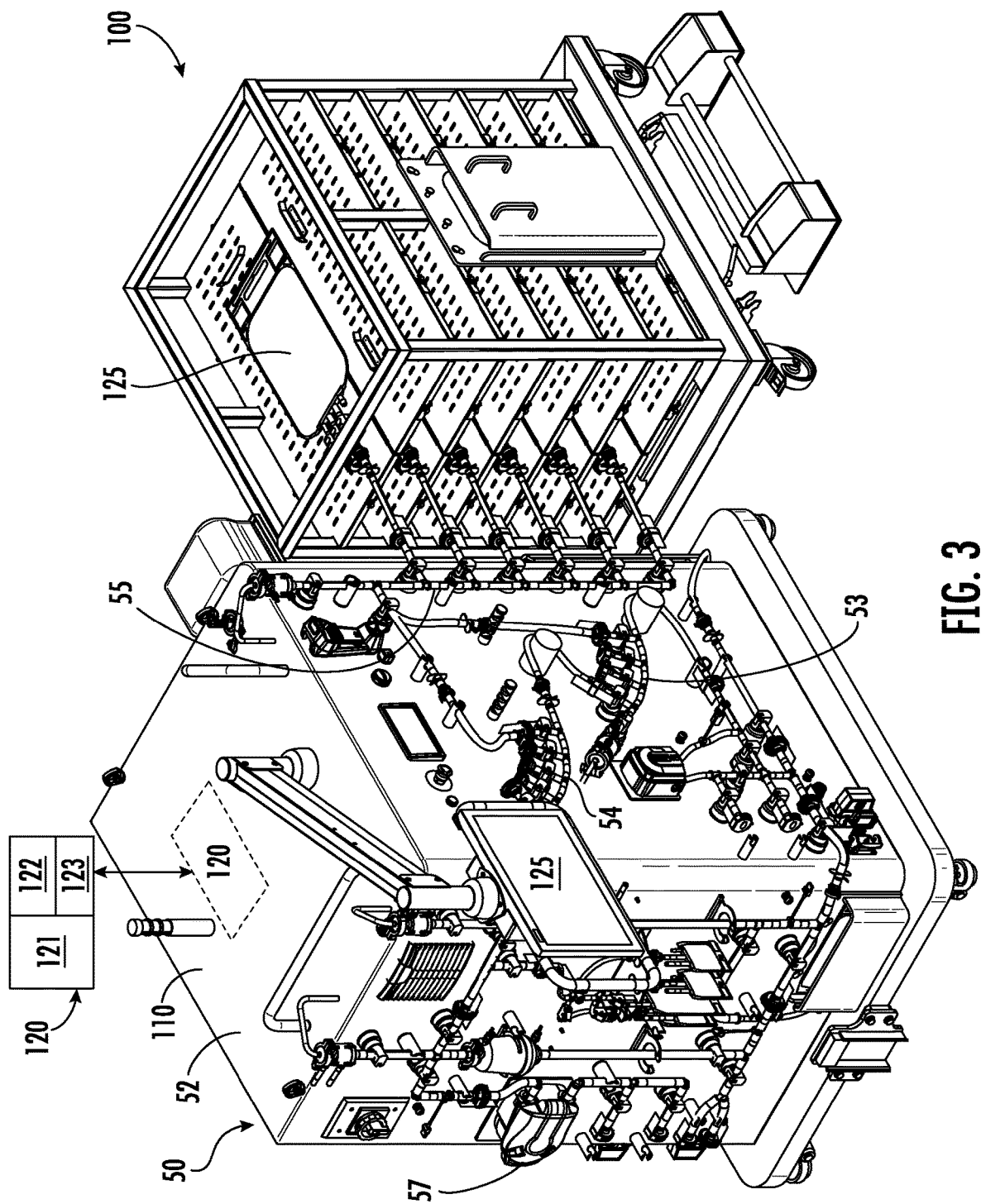
FIG. 3 is another perspective elevational view of the distributor skid of FIG. 1 and a perspective view of an embodiment of a workstation configured to hold a plurality of single use containers for receiving aliquoted portions of fluid from the fluid distribution system.

The valves of the first filler valve arrangement 93 are disposed along a vertical axis in spaced relationship to each other. The single use filler manifold 55 is mounted to the distributor skid 52 such that the valves of the first filler valve arrangement 93 are respectively associated with each one of the filler manifold outlets. This arrangement is particularly useful in filling containers stored in a workstation 100 configured as shown in FIG. 3.

Figure 5:
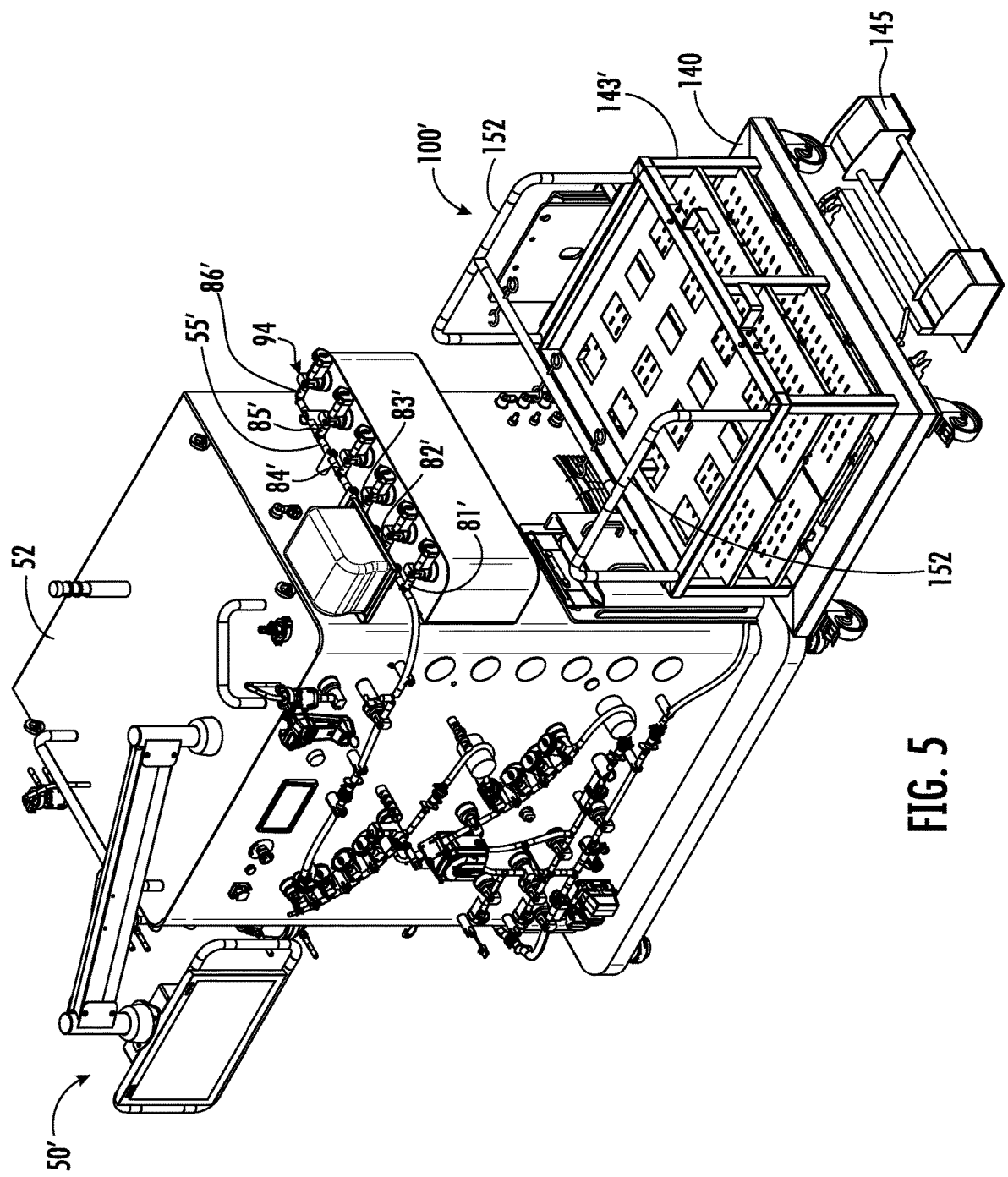
FIG. 5 is another perspective elevational view of the distributor skid of FIG. 1, including another embodiment of a fluid distribution system constructed in accordance with principles of the present disclosure, and a perspective view of another embodiment of a workstation configured to hold a plurality of single use containers for receiving aliquoted portions of fluid from the fluid distribution system.

The valves of the second filler valve arrangement 94 are disposed along a horizontal axis in spaced relationship to each other. A single use filler manifold 55' as shown in FIG. 5 can be mounted to the distributor skid 52 such that the valves of the second filler valve arrangement 94 are respectively associated with each one of the filler manifold outlets. This arrangement is particularly useful in filling containers stored in a workstation 100' configured as shown in FIG. 5.

Referring to FIG. 2, in embodiments, the fluid distribution system 50 can include means for removing air trapped within the manifolds 53-55 to enhance the accuracy and consistency of the fluid dispensing process. In the illustrated embodiment, an air filter 96 and a vent conduit 97 are provided. The vent conduit 97 is in fluid communication with the manifolds 53-55 via a vent junction 98 associated with the single use filler manifold 55. The air filter 96 is in fluid communication with the body conduit of the filler manifold 55 and the body conduits of the upstream and intermediary single use distributor manifolds 53, 54 via the vent conduit 97.

In embodiments, the air filter 96 is configured to filter particulate. In embodiments, the air filter 96 presents a sterile barrier between the product fluid inside the manifolds and the surrounding atmosphere. It is basically preventing non-sterile air coming into the manifold flow path at any point during installation or processing The vent conduit 97 includes a vent liquid sensor 99 and a vent valve 101 to protect the air filter 96 from exposure to liquid. The vent liquid sensor 99 is configured to generate a liquid detection signal in response to detecting liquid in the vent conduit 97. The control unit 120 is in electrical communication with the vent liquid sensor 99 to receive the liquid detection signal therefrom. The vent valve 101 is arranged with the vent conduit 97 to selectively occlude the vent conduit 97. The vent valve 101 is interposed between the vent liquid sensor 99 and the air filter 96. The vent liquid sensor 99 is interposed between the vent junction 98 and the vent valve 101. The vent valve 101 is in operable arrangement with the control unit 120 such that the control unit can selectively operate the vent valve 101. In embodiments, the control unit 120 is configured to cease operation of the pump(s) 57 and/or close the vent valve 101 in response to receiving the liquid detection signal to prevent the filter 96 from becoming wetted with fluid during distribution manifold priming.

In embodiments, the control unit 120 is configured to perform a priming operation. In embodiments, the control unit 120 is configured to open the vent valve 101 to open the vent conduit 97, operate the pump(s) 57 to deliver the flow of fluid to the single use filler manifold 55 with all of the filler manifold outlets 81-86 closed such that the body of the filler manifold 55 is filled with fluid and such that air in the manifolds 53-55 is displaced to the vent conduit 97 via the vent junction 98. The control unit 120 can be configured to cease operation of the pump(s) 57 and/or close the vent valve 101 in response to receiving the liquid detection signal, thereby indicating the body of the single use filler manifold 55 is filled up with fluid above the vent junction 98.

In embodiments, the vent junction 98 is located at a relative high point of the series of manifolds 53-55 fluidly connected together. In embodiments, the distributor manifolds 53, 54 are configured such that fluid moves therethrough toward the filler manifold 55 in a substantially uphill trajectory from the upstream distributor manifold inlet 60 to the filler manifold inlet 80 and, in embodiments, to the vent junction 98. In embodiments, the bodies of the distributor manifolds 53, 54 extend along a line an inclined path that is at least 0.5° to the horizontal axis. The control unit 120 can be configured such that as liquid is introduced into the upstream distributor manifold inlet 60 and flows through the manifolds 53-55, the liquid replaces the air from the current flowpath pushing it to the air filter 96 and out of the series of manifolds 53-55 during the priming operation.

In embodiments, the control unit 120 is configured to perform an underfilling operation. In embodiments, the control unit 120 is configured to feed the supply of fluid into the filler manifold inlet 80 of the single use filler manifold 55 and sequentially discharge a target fill volume of fluid respectively from each standard fill outlet 81-85 of the single use filler manifold 55 into the single use containers respectively aseptically fluidly connected thereto. After sequential target fill volume discharging, an underfill volume of fluid is discharged from the underfill outlet 86 of the single use filler manifold 55 to the single use container aseptically fluidly connected thereto. In embodiments, the underfill volume is less than the target fill volume. In embodiments, the underfill volume combined with the volume of fluid drained from the filler manifold 55 is substantially the same as the target fill volume. In embodiments, the underfill outlet 86 of the single use filler manifold 55 can be the outlet that is lowest in the direction of the effect of gravity.

After underfill volume discharging, the control unit 120 can be configured to drain the fluid from the body conduit of the filler manifold 55 out of the underfill outlet 86 into the single use container aseptically fluidly connected thereto. The control unit 120 can be configured to open the vent valve 101 during draining.

In embodiments, a filler manifold drain valve 102 can be provided upstream of the vent junction 98 to selectively occlude the filler manifold inlet 80 during the filler manifold draining operation to further promote the draining of the fluid from the body of the filler manifold 55 out the underfill outlet 86. The filler manifold drain valve 102 is in operable arrangement with the control unit 120 such that the control unit can selectively operate the filler manifold drain valve 102. In embodiments, the control unit 120 is configured to close the filler manifold drain valve 102 during filler manifold draining to help maintain consistency in the volume of fluid drained from the filler manifold 55 during the draining operation.

In embodiments, a low drain liquid sensor 103 can be associated with the body of the filler manifold 55 near and above the underfill outlet 86 such that a fluid level in the body of the filler manifold 55 can be monitored to help determine when the filler manifold draining operation is complete. The low drain liquid sensor 103 is configured to generate a low filler manifold drain liquid signal in response to detecting liquid in the filler manifold 55 is below a predetermined low level, corresponding to completion/near completion of the draining operation.

The control unit 120 is in electrical communication with the low drain liquid sensor 103 to receive the low filler manifold drain liquid signal. In embodiments, the control unit 120 can be configured to stop the filler manifold drain operation in response to receiving the low filler manifold drain liquid signal. In embodiments, the control unit 120 can be configured to open the filler manifold drain valve 102 and to close the vent valve 101 in response to receiving the low filler manifold drain liquid signal. The location of the low drain liquid sensor 103 can help ensure that the filler manifold draining operation stops before all fluid is drained from the filler manifold 55 to help prevent air from also being delivered to the single use container connected to the underfill outlet 86.

In embodiments, the fluid distribution system 50 can include means for recovering fluid from one or more of the manifolds 53-55 that would otherwise be retained in the manifolds 53-55 or not be discharged into the single use containers filled during the filling operations. In the illustrated embodiment, the fluid distribution system 50 includes means for recovering fluid from one or more of the distributor manifolds 53, 54 comprising a recovery conduit 106, a recovery container 107, and a recovery pump 108.

The recovery conduit 106 comprises an aseptic fluid reserve pathway, that is in fluid communication with the distributor manifolds 53, 54 and is adapted to be placed in fluid communication with the recovery container 107 (see also FIG. 1). The recovery conduit 106 includes a recovery valve 109. The recovery valve 109 is arranged with the aseptic fluid reserve pathway 106 such that the aseptic fluid reserve pathway 106 is occludable via the recovery valve 109. The recovery valve 109 is in operable arrangement with the control unit 120 such that the control unit 120 can selectively operate the recovery valve 109.

The recovery container 107 can be placed in fluid communication with the distributor manifold(s) 53, 54 via the aseptic fluid reserve pathway provided by the recovery conduit 106. A recovery container storage compartment 116 is mounted to the distributor skid 52 (see also FIG. 1). The recovery container storage compartment 116 is configured to receive the recovery container 107 therein. The recovery container storage compartment 116 is positioned such that the recovery container 107 is disposed below, in the direction gravity acts upon the fluid in the distributor manifolds 53, 54, the distributor manifolds 53, 54 and the air filter 96.

Figure 13:
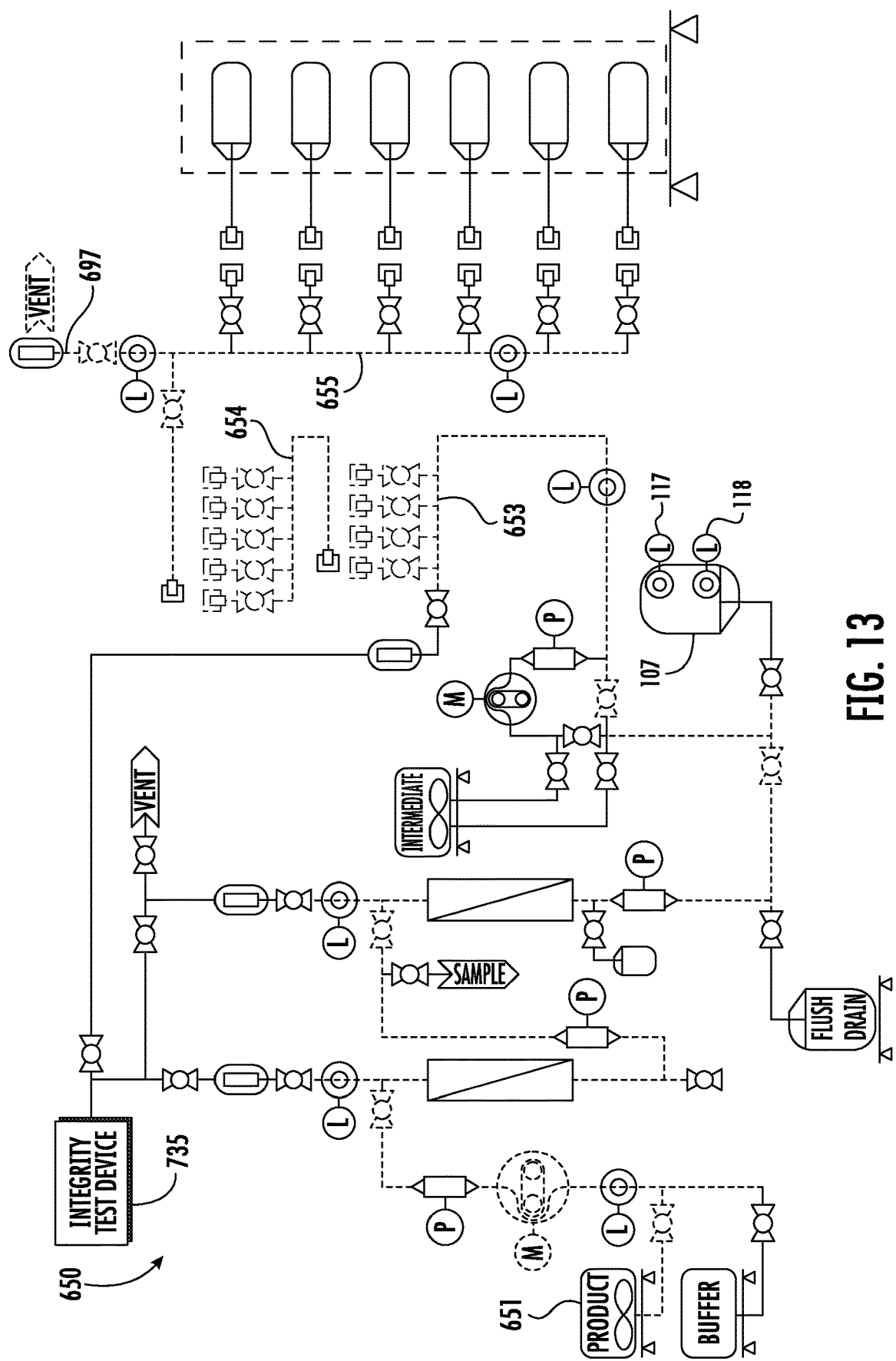
FIGS. 13-21 are schematic diagrams of an embodiment of a fluid distribution system constructed in accordance with principles of the present disclosure, illustrating a series of fluid recovery steps of an embodiment of a method of aseptically distributing fluid following principles of the present disclosure.

A recovery high liquid sensor 117 and a recovery low liquid sensor 118 can be associated with the storage compartment 116 such that a respective, predetermined maximum and minimum fluid volume in the recovery container can be monitored (see also FIG. 13) to help avoid overfilling the recovery container and/or inadvertently drawing air into the system. Referring to FIG. 13, the recovery high liquid sensor 117 is arranged with the recovery container 107 and is configured to generate a high recovery liquid level signal in response to detecting liquid in the recovery container 107 at a predetermined high level, corresponding to a predetermined maximum fluid volume in the recovery container. The recovery low liquid sensor 116 is arranged with the recovery container 107 and is configured to generate a low recovery liquid level signal in response to detecting liquid in the recovery container 107 is below a predetermined low level, corresponding to a predetermined minimum fluid volume in the recovery container. The control unit 120 is in electrical communication with the high and low recovery liquid sensors 117, 118 to receive, respectively, the high and low recovery liquid level signals therefrom.

Referring to FIG. 2, in embodiments, the recovery pump 108 is in fluid communication the recovery container 107 via the recovery conduit 106 and a fluid supply conduit 119 fluidly connected to the upstream distributor manifold inlet 60. The recovery pump is adapted to selectively produce a flow of recovery fluid from the recovery container to the upstream distributor manifold inlet 60 to comprise part of the supply of fluid distributed through the manifolds 53-55.

In embodiments, the control unit 120 can be configured to automatically drain fluid from the distributor manifolds 53, 54 through the recovery conduit 106 to the recovery container 107. In embodiments, the control unit 120 is configured to open the vent valve 101 to admit air from outside the air filter 96 into the distributor manifolds 54, 53, and to open the recovery valve 109. In embodiments, the control unit 120 can be configured to close the vent valve 101 and to close the recovery valve 109 in response to receiving the high recovery liquid level signal to stop a distributor manifold fluid draining operation. In embodiments, a recovery liquid sensor can be provided in the recovery conduit 106 upstream of the recovery container 107 to provide the control unit a signal when the recovery level sensor detects no more fluid passing through the recovery conduit 106 to the recovery container 107 so that the control unit 120 can stop the distributor manifold draining operation.

In embodiments, the control unit 120 can be configured to automatically introduce fluid from the recovery container 107 back into the series of manifolds 53-55 during a priming operation. In embodiments, the control unit 120 can be configured to operate the recovery pump 108 to draw recovery fluid from the recovery container 107 to the upstream distributor manifold inlet 60. In embodiments, the control unit 120 can be configured to feed the supply of fluid into the upstream distributor manifold inlet 60 by introducing recovery fluid from the recovery container 107 such that at least a portion of the supply of fluid comprises recovery fluid from the recovery container 107. In embodiments, the control unit 120 can be configured to operate the recovery pump 108 and at least one other pump 57 during the priming operation. In embodiments, the control unit 120 can be configured to cease operation of the recovery pump 108 during a fluid priming operation in response to receiving the low recovery liquid level signal.

Referring to FIG. 1, the distributor skid 52 includes a trolley 105, a cabinet 110, the single use manifolds 53-55, and the valve arrangements 91-94. The cabinet 110 is mounted atop the trolley 105 and is configured to house hydraulic and automation equipment of the liquid distribution system 50. The manifolds 53-55 comprise single use manifolds that are removably mounted to the cabinet 110 such that the manifolds 53-55 are is in operable arrangement with the valves of the valve arrangements 91-93 mounted to the cabinet 110.

The trolley 105 includes a base 112 and a plurality of wheels 114 rotatably attached to the base 112. In the illustrated embodiment, the base 112 is rectangular, and there is a wheel 114 rotatably attached at each corner of the base 112. In embodiments, the base 112 can be substantially square-shaped.

The cabinet 110 is mounted to the base 112 of the trolley 105. In embodiments, the cabinet 110 comprises a storage unit for automation and hydraulic equipment and is made from a suitable metal, such as stainless steel, for example. The cabinet 110 defines an interior cavity which can be suitably configured for storing and supporting components of the liquid distribution system. The valves of the valve arrangements 91-94 can be supported by the cabinet 110. In the illustrated embodiment, a clamping portion of each valve projects from an exterior surface of the cabinet 110 for being respectively associated with a manifold outlet.

Referring to FIG. 3, in embodiments, the cabinet 110 houses therein the control unit 120 and at least one pump body 57. The pump 57 is in operable relationship with the control unit 120 such that the control unit 120 can selectively operate the pump 57. The pump 57 is adapted to selectively produce a flow of fluid to deliver a supply of fluid to the manifolds 53-55. In embodiments, the pump 57 can be any suitable pump capable of producing a flow of fluid through the manifolds for delivery to the single use containers 125 connected to the filler manifold 55 and that meets the specification of the intended application. In embodiments, the pump 57 comprises a variable displacement pump. In embodiments, the fluid distribution system 50 includes a plurality of pumps which can be used to delivery one or more types of fluid to the manifolds 53-55.

In embodiments, the control unit 120 can comprise any suitable equipment configured to control the operation of at least one component of the liquid distribution system 50 when performing a filling operation. In embodiments, the control unit 120 includes a processor 121, a non-transitory computer readable medium 122 bearing a fluid distribution program, a data storage device 123, and a display device 125. The processor 121 is arranged with the computer readable medium 122 to execute the fluid distribution program. The processor 121 is in operable arrangement with the display device 125 to selectively display output information from the fluid distribution program and/or to receive input information from a graphical user interface displayed by the display device 125.

The processor 121 can be configured to act as a controller to selectively operate at least one component of the fluid distribution system 50, such as the pump 57 and the valve arrangements, for example. In embodiments, the processor 121 is in electrical communication with the pump(s) and the valve arrangements to selectively operate the valves based upon instructions from the fluid distribution program.

In embodiments, a controller and the processor 121 can comprise separate devices, and the controller can be in operable communicative arrangement with the processor 121. In embodiments, the controller can include a user input and/or interface device having one or more user-actuated mechanisms (e.g., one or more push buttons, slide bars, rotatable knobs, a keyboard, and a mouse) adapted to generate one or more user actuated input control signals. In embodiments, the controller can be configured to include one or more other user-activated mechanisms to provide various other control functions for the fluid distribution system, as will be appreciated by one skilled in the art. The controller can be associated with the display device 125 which is adapted to display a graphical user interface. The graphical user interface can be configured to function as both a user input device and a display device in embodiments. In embodiments, the display device 125 can comprise a touch screen device adapted to receive input signals from a user touching different parts of the display screen. In embodiments, the controller can be in the form of a smart phone, a tablet, a personal digital assistant (e.g., a wireless, mobile device), a laptop computer, a desktop computer, or other type of device.

In embodiments, the fluid distribution program has a scaling module configured to sequentially progress through a series of valve open-closed conditions to carry out a filling sequence according to principles of the present disclosure. For example, the scaling module can be configured to open a respective one of the upstream distributor manifold outlets and the intermediary distributor manifold outlets and close the other of upstream distributor manifold outlets and the intermediary distributor manifold outlets to perform a corresponding sequential series of filling operations with a respective one of the set of single use filler manifolds. The scaling module can sequence through an open condition for each one of the intermediary distributor manifold outlets with the one of the upstream distributor manifold outlets in the open condition, and then close that one of the upstream distributor manifold outlets and put a second one of the upstream distributor manifold outlets in the open condition while the others are closed. The scaling module can orchestrate sequential filling operations for the rest of the valves in a similar manner. In embodiments, the scaling module includes logic for scaling the filling operations to a desired number of containers for a filling sequence for a given closed system.

In embodiments, the fluid distribution program is configured to perform at least one fluid recovery operation for efficiently using fluid that would otherwise be retained in the manifolds 53-55 or not be discharged into the single use containers filled during the filling operations. In embodiments, the fluid distribution program is configured to perform at least one of a fluid recovery operation in the form of a single use container underfill operation, a manifold draining operation, and a manifold priming operation.

For example, in embodiments, the fluid distribution program includes a container filling module configured to automatically perform at least one fluid recovery operation. In embodiments, the fluid distribution program includes a container filling module configured to perform a fluid recovery operation in the form of a single use container underfill operation. In embodiments, the container filling module is configured to perform a single use container underfill operation including discharging a target fill volume of the supply of fluid out of each standard fill outlet 81-85 of the filler manifold outlets 81-86, discharging an underfill volume of the supply of fluid out of the underfill outlet 86 of the filler manifold outlets 81-86, and draining a filler manifold volume of the supply of fluid from the filler manifold body conduit of the single use filler manifold 55 out of the underfill outlet 86 of the filler manifold outlets 81-86. The underfill volume is less than the target fill volume. In embodiments, the underfill volume combined with the filler manifold volume is substantially the same as the target fill volume.

In embodiments, the container filling module is configured to perform a single use container underfill operation including feeding the supply of fluid into the filler manifold inlet 80 of the single use filler manifold 55. The target fill volume of the fluid is sequentially discharged respectively from each standard fill outlet 81-85 of the filler manifold outlets 81-86 into the single use containers respectively aseptically fluidly connected thereto. After sequential target fill volume discharging, the underfill volume of fluid is discharged from the underfill outlet 86 to the single use container aseptically fluidly connected to it. After underfill volume discharging, the filler manifold volume of fluid is drained from the filler manifold body conduit 55 out of the underfill outlet 86 into the single use container aseptically fluidly connected thereto. In embodiments, the underfill portion and the filler manifold volume are together in combination substantially the same as the fill portion. In embodiments, the vent valve 101 is opened during draining to facilitate the draining of fluid from the body conduit of the filler manifold 55. In embodiments, the container filling module is configured to discharge the fill portions at substantially the same time.

In embodiments, the fluid distribution program is configured to perform a fluid recovery operation in the form of a manifold draining operation. In embodiments, the fluid distribution program includes a distributor manifold draining module configured, when executed by the processor, to drain fluid from at least one distributor manifold 53, 54 into the aseptic fluid reserve pathway 106 to the recovery container 107. In embodiments, draining distributor manifold fluid includes draining fluid remaining in both the upstream single use distributor manifold 53 and the intermediary single use distributor manifold 54. In embodiments, draining the distributor manifold fluid includes opening the vent valve 101, and opening at least one recovery valve 109 arranged with the recovery conduit 106. In embodiments, the distributor manifold draining module is configured, when executed by the processor, in response to receiving the high recovery liquid level signal, to close the vent valve 101, and to close the recovery valve 109 arranged with the recovery conduit 106.

In embodiments, the fluid distribution program is configured to perform a fluid recovery operation in the form of a manifold priming operation. In embodiments, the fluid distribution program includes a filler manifold priming module configured to a fluid recovery operation in the form of a manifold priming operation. In embodiments, the fluid distribution program includes a filler manifold priming module configured to prime the filler manifold body conduit of the single use filler manifold with a supply of fluid that fills the body of the filler manifold. In embodiments, the filler manifold priming module is configured to open the vent valve 101 to displace air in the filler manifold body conduit out of the air filter 96 during priming and to place the vent valve 101 in the closed position after the filler manifold body is primed.

In embodiments, the filler manifold priming module is configured to prime the manifold(s) by introducing recovery fluid from the recovery container 107 into the distributor manifold inlet 60 via the aseptic fluid reserve pathway 106 such that at least a portion of the supply of fluid comprises recovery fluid from the recovery container 107. In embodiments, the filler manifold priming module is configured to operate the recovery pump 108 to draw recovery fluid from the recovery container 107 during the manifold priming operation. In embodiments, the filler manifold priming module is configured, in response to receiving the low recovery liquid level signal, to cease operation of the recovery pump, and to close the recovery valve arranged with the recovery fluid fill pathway 106.

In embodiments, the control unit 120 is in electrical communication with each pump 57, 107 used to deliver the fluid(s) to the manifolds 53-55 and with each valve of the valve arrangements 91-94. The control unit 120 is configured to selectively operate the pump 57 and the valves of the valve arrangements 91-94 according to logic and operation parameters contained in the fluid distribution program. In embodiments, the control unit 120 is configured to control at least one of a pump speed and a volume displacement of the pump 57 to control the amount of fluid being dispensed into the single use containers 125 connected to the filler manifold 55. In the illustrated embodiment, the control unit 120 is configured to independently operate each valve of the different valve arrangements 91-93 to place each valve arrangement in a series of sequential valve conditions in order to fill a number of single use containers 125 that is greater than the number of filler manifold outlets of any one of the set of single use filler manifolds 55.

In embodiments, the control unit 120 is configured to selectively operate the pump(s) 57 according to at least one input signal received from each workstation 100 holding the containers 125. In embodiments, the control unit 120 is configured to operate the distributor skid 52 to perform at least one filling sequence.

In embodiments, the processor 121 comprises a specially programmed processor that can be used to fill a series of single use containers 125 using at least one distributor manifold 53, 54 and a set of single use filler manifolds 55. In the illustrated embodiment, the processor 121 is configured to facilitate the control and the operation of the fluid distribution system 50. In embodiments, the processor 121 can be configured to receive input signals from the controller, to send input control signals to the controller, and/or to send output information to the controller. In the illustrated embodiment, the controller and the processor 121 comprise the same device.

In embodiments, the processor 121 is configured to display in the display device 125 fluid data received from at least one sensor in electrical communication with the control unit 121. The fluid data can also be stored in the data storage device 123 operably arranged with the processor 121.

In embodiments, the processor 121 can comprise any suitable computing device, such as, a microprocessor, a mainframe computer, a digital signal processor, a portable computing device, a personal organizer, a device controller, a logic device (e.g., a programmable logic device configured to perform processing functions), a digital signal processing (DSP) device, or a computational engine within an appliance. In embodiments, the processor 121 also includes one or more additional input devices (e.g., a keyboard and a mouse).

The processor 121 can have one or more memory devices associated therewith to store data and information. The one or more memory devices can include any suitable type, including volatile and non-volatile memory devices, such as RAM (Random Access Memory), ROM (Read-Only Memory), EEPROM (Electrically-Erasable Programmable Read-Only Memory), flash memory, etc. In one embodiment, the processor 121 is adapted to execute programming stored upon the non-transitory computer readable medium 122 to perform various methods, processes, and modes of operations in a manner following principles of the present disclosure.

In embodiments, the non-transitory computer readable medium 122 can contain a fluid distribution program that is configured to implement an embodiment of a method of distributing fluid according to principles of the present disclosure. In embodiments, the fluid distribution program includes a graphical user interface that can be displayed by the display device 125. The graphical user interface can be used to facilitate the inputting of commands and data by a user to the fluid distribution program and to display outputs generated by the fluid distribution program.

The fluid distribution program can be stored upon any suitable computer-readable storage medium. For example, in embodiments, a fluid distribution program following principles of the present disclosure can be stored upon a hard drive, floppy disk, CD-ROM drive, tape drive, zip drive, flash drive, optical storage device, magnetic storage device, and the like.

In embodiments, the processor 121 is in operable communication with the data storage device 123 which includes at least one database containing fluid distribution data. In embodiments, the fluid distribution program can be configured to store the fluid distribution data generated during operation of the system in the data storage device 123. In embodiments, the fluid distribution data can be associated in a logical manner with time data in the data storage device such that the various data can be retrievable for a given time.

Figure 4:
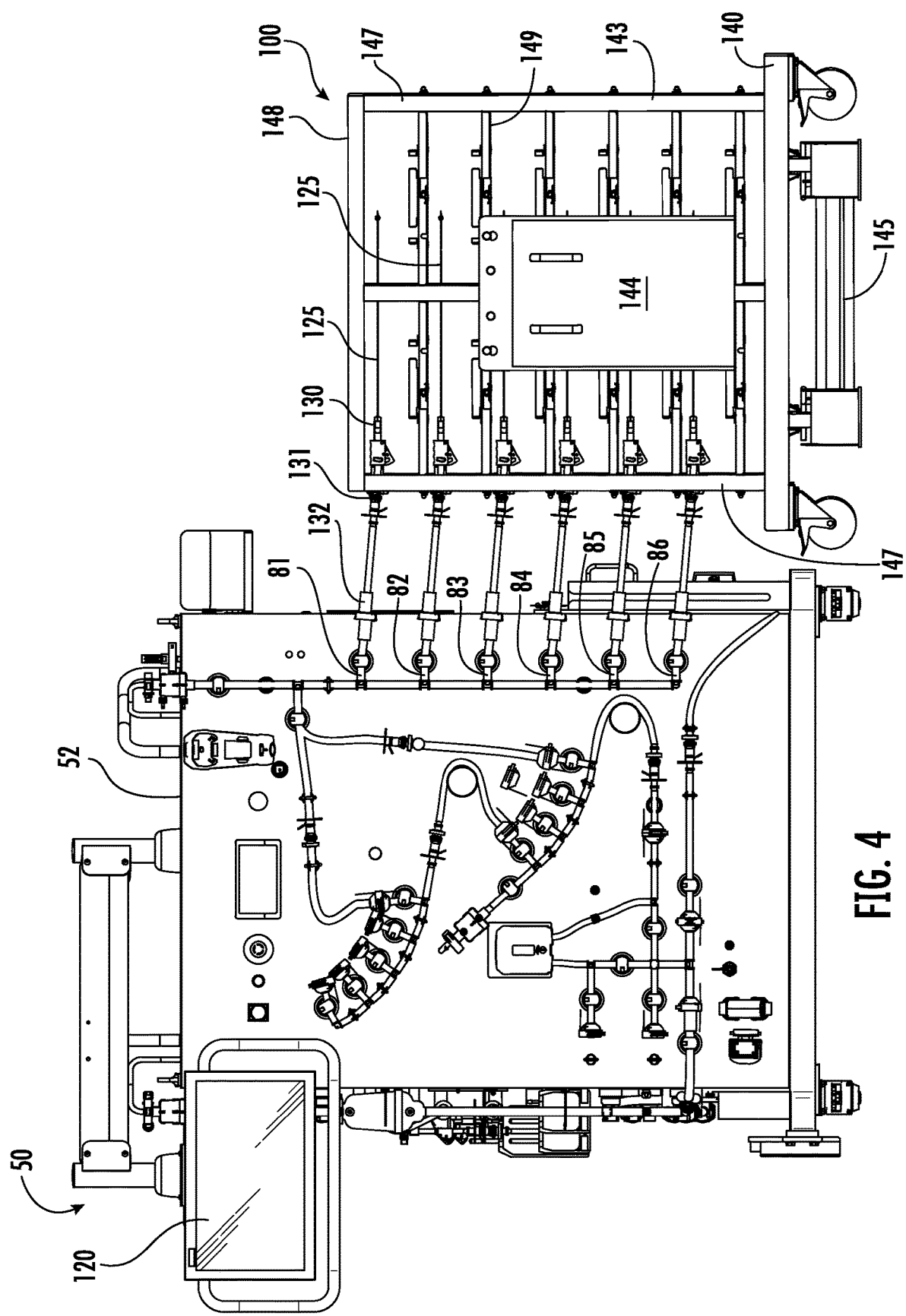
FIG. 4 is an elevational view of the distributor skid and the workstation of FIG. 4.

Referring to FIG. 4, the workstation 100 is configured to hold a plurality of single use containers 125. Each single use container 125 has an access port 130 which is fluidly connected to a respective one of the filler manifold outlets 81-86 via an aseptic fluid disconnector 131 and an aseptic fluid connector 132.

The workstation 100 comprises a workstation configured to hold fluid in the singles use containers 125 that the fluid distribution system aliquoted from a larger supply. The workstation 100 includes a trolley 140, a frame structure 143, a recovery container storage compartment 144, and a weigh scale 145.

The frame structure 143 is mounted to the trolley 140 and is configured to support the single use containers 125 in a stacked relationship. The frame structure 143 includes four uprights 147 connected to a respective corner of the trolley 140 and in spaced relationship to each other and four cross members 148 each extending between two of the uprights 147 such that the frame structure 143 has a rectangular configuration. In the illustrated embodiment, the workstation includes six shelves 149 that are each configured to support at least one single use container 125 such that the frame structure 143 can support single use containers 125 in a vertical stacked relationship to each other. In other embodiments, the workstation 100 can be configured to support a different number of single use containers 125, including having shelves 149 each configured to support multiple single use containers 125.

The recovery container storage compartment 144 is mounted to the frame structure 143 and is configured to receive therein the recovery container 107. In embodiments, once the closed system is opened after performing scaled filling operations using the manifolds 53-55 connected in series, the recovery container 107 can be disconnected from the recovery conduit 106 and stored in the recovery container storage compartment 144 mounted to the frame structure 143. The "odd" volume of fluid remaining in the recovery container 107 can be associated with the single use containers filled during the use of this particular recovery container 107. Rather than generating an odd volume during the filling operation performed using each one of the set of single use filler manifolds 55, the recovery container 107 can be the only odd volume produced after using all of the sets of filler manifolds 55.

The trolley 140 includes a base and a plurality of wheels rotatably attached to the base. In the illustrated embodiment, the base is rectangular, and there is a wheel rotatably attached at each corner of the base. In embodiments, the base can be substantially square-shaped. The base of the trolley 140 is mounted to a bottom of the frame structure 143. The trolley 140 is positionable over the weigh scale 145 such that the weigh scale 145 supports the weight of the trolley 140 (and thus also the frame structure 143 and the containers 125 stored therein).

In embodiments, the weigh scale 145 can be any suitable scale suitable for weighing loads in a range corresponding to the intended fluid application. In embodiments, the weigh scale 145 comprises a suitable load cell which generates an electrical signal indicative of the measured weight. The weigh scale 145 can be configured to generate a weight signal and can be placed in electrical communication with the control unit 120 to transmit the weight signal to the control unit 120. The control unit 120 can use the weight signal to provide a feedback loop to the control unit 120 to verify the intended amount of fluid is dispensed to the containers 125 stored in the workstation 100. In embodiments, the control unit 120 can be configured to convert the measured weight of the fluid into a volume measurement for such fluid.

In other embodiments, a workstation suitable for use with a fluid distribution system constructed according to principles of the present disclosure can have a different construction. For example, in other embodiments, the volume/weight of the containers 125 can be monitored using other techniques, as will be appreciated by one skilled in the art, such as a fill level sensor. In embodiments, the fill level sensor is configured to generate a fill level signal indicative of the amount of material within the storage volume of the single use container as detected by the fill level sensor. Each fill level sensor can be place in electrical communication with the control unit so that the control unit can use the fill level signals as a feedback loop. In embodiments, a capacitive fill level sensor can be used to measure the fill level of fluid media or of solid materials disposed within the storage volume of the container. In embodiments, the capacitive fill level sensor can be a suitable commercially-available strip sensor, such as those available from Balluff Ltd., which can detect fill levels along the strip over a predetermined length, such as, e.g., 850 mm. In embodiments, the capacitive fill level sensor for measuring fill levels can be configured to develop a measurement impedance in response to being within detection proximity of the material stored within the single use container, the ohmic component of which, particularly the capacitive component of which, reflects a measure for the fill level of the material within the container and which can be used to generate the fill level signal.

Each of the single use containers 125 is in fluid connection with a respective one of the filler manifold outlets 81-86 of the distributor skid 52 via a flexible tubing line extending between each container 125 and the filler manifold outlet 81-86 with which it is associated, and in which fluid communication is selectively maintained via a respective aseptic connector 132. In embodiments, the aseptic connector 132 can be any suitable connector, such as commercially-available aseptic connectors which will be familiar to those skilled in the art. In embodiments, the tubing which places the containers 125 in fluid communication with the associated filler manifold outlet 81-86 is adapted to be selectively occluded by a pinch valve externally mounted thereto and, in embodiments, comprises flexible tubing made from any suitable material, such as, silicone, thermoplastic elastomer (TPE), etc.

In embodiments, the single use container 125 comprises any suitable container configured to store a predetermined volume of material for use in an intended application. In embodiments, the single use container 125 comprises a "2D" (or "two-dimensional") biocontainer bag, as is familiar to those skilled in the art.

In the illustrated embodiment, the single use container 125 comprises a 2D biocontainer bag made from a flexible film material. The biocontainer bag 125 can include two or more ports and tubing with connector ends that are configured to receive material within the interior storage volume of the bag and/or discharge material from the bag. In other embodiments, the biocontainer bag 125 includes at least one other port configured for use as a sampling port. In embodiments, the biocontainer bag 125 can define therein a storage volume of a predetermined size, such as a volume in a range from one liter to twenty liters, for example. In other embodiments, the storage volume can be a different size, such as, e.g., one hundred liters. In embodiments, the biocontainer bag 125 comprises a suitable commercially-available single use biocontainer bag, such as, for example, those available from Pall Corporation of Port Washington, N.Y., under the brand name Allegro™ 2D biocontainer bags.

In embodiments, the biocontainer bag 125 can include at least a pair of flexible panels that are connected together. The flexible panels cooperate together to define an interior storage volume that is configured to hold a predetermined volume of material (e.g., one hundred liters). In embodiments, each panel is made from a suitable plastic material. For example, in embodiments, each panel is made of a low density polyethylene (LDPE) fluid contact and external film with an ethylene-vinyl alcohol copolymer (EvOH) gas barrier internal film. In embodiments, the biocontainer bag can be made from a material that satisfies the requirements of at least one of: the USP <88> Biological Reactivity Tests, in vivo, for Class VI-50° C. Plastics that target-monitor the effect of the biocontainer's extracts for their systemic toxicity, tissue irritation, and biocompatibility for implantation; USP <87> Biological Reactivity Tests (in vitro) for plastics (cytotoxicity); and ISO 10993 Biological Evaluation of a Medical Device (Section 8.2.2: ISO 10993 Biological Evaluation of Medical Devices) in Section 4 (Hemolysis), Section 5 (Cytotoxicity), Section 6 (Implantation Test), Section 10 (Irritation and Sensitization Test), and Section 11 (Acute Systemic Toxicity).

Referring to FIG. 5, in embodiments, the fluid distribution system 50' includes a single use filler manifold 55' mounted to the distributor skid 52 such that the valves of the second filler valve arrangement 94 are respectively associated with each one of the filler manifold outlets 81', 82', 83', 84', 85', 86'. The valves of the second filler valve arrangement 94 are disposed in spaced relationship to each other along the horizontal axis. With this arrangement, the filler manifold outlets 81'-86' can be disposed over a workstation 100' configured as shown in FIGS. 5 and 6.

Figure 6:
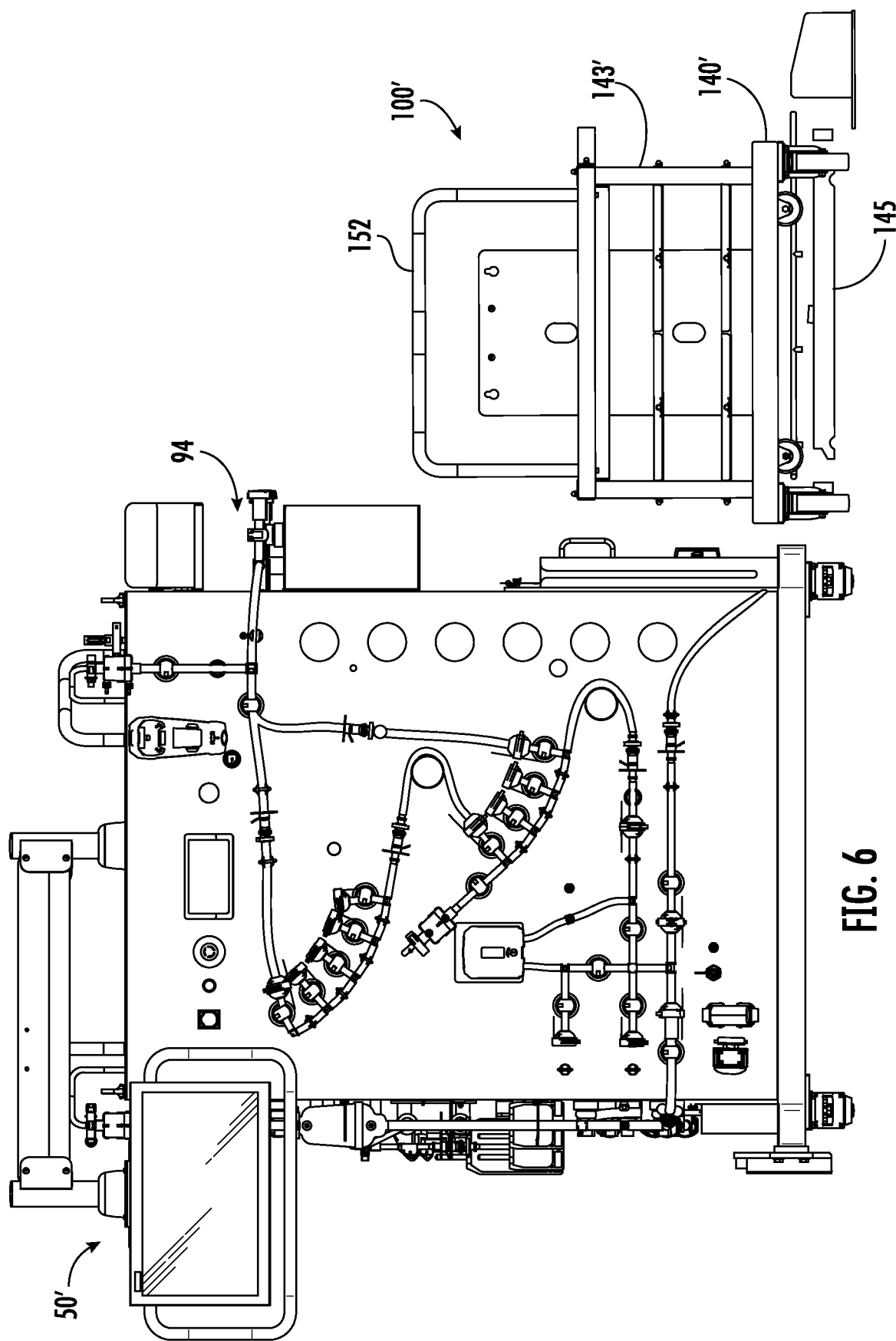
FIG. 6 is an elevational view of the distributor skid and the workstation of FIG. 5.
Figure 7:
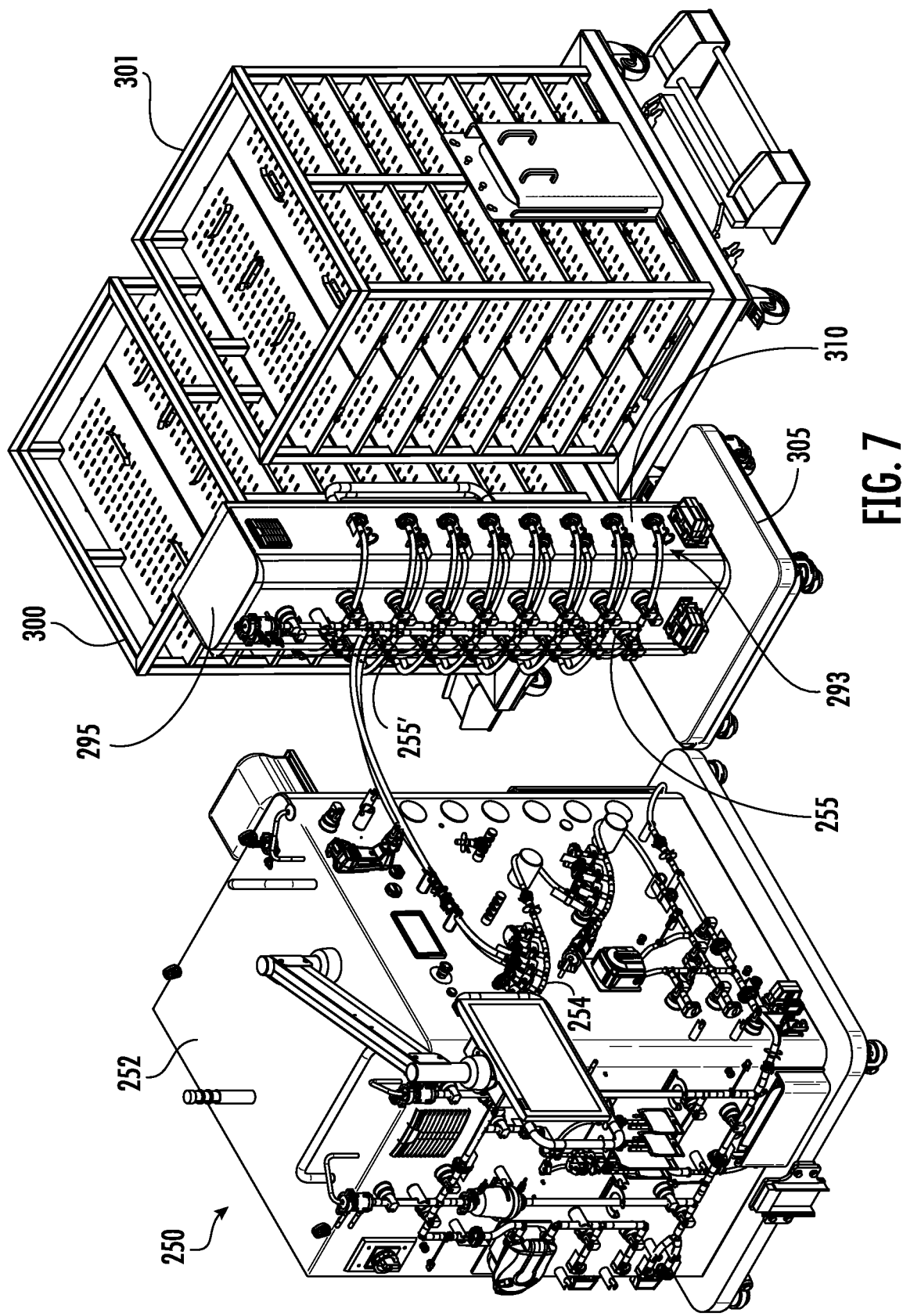
FIG. 7 is a perspective view of another embodiment of a fluid distribution system constructed in accordance with principles of the present disclosure, including a distributor skid and an embodiment of a distribution tower having a single use filler manifold of the fluid distribution system mounted thereto, and a perspective view of another embodiment of a workstation configured to hold a plurality of single use containers for receiving aliquoted portions of fluid from the fluid distribution system.
Figure 8:
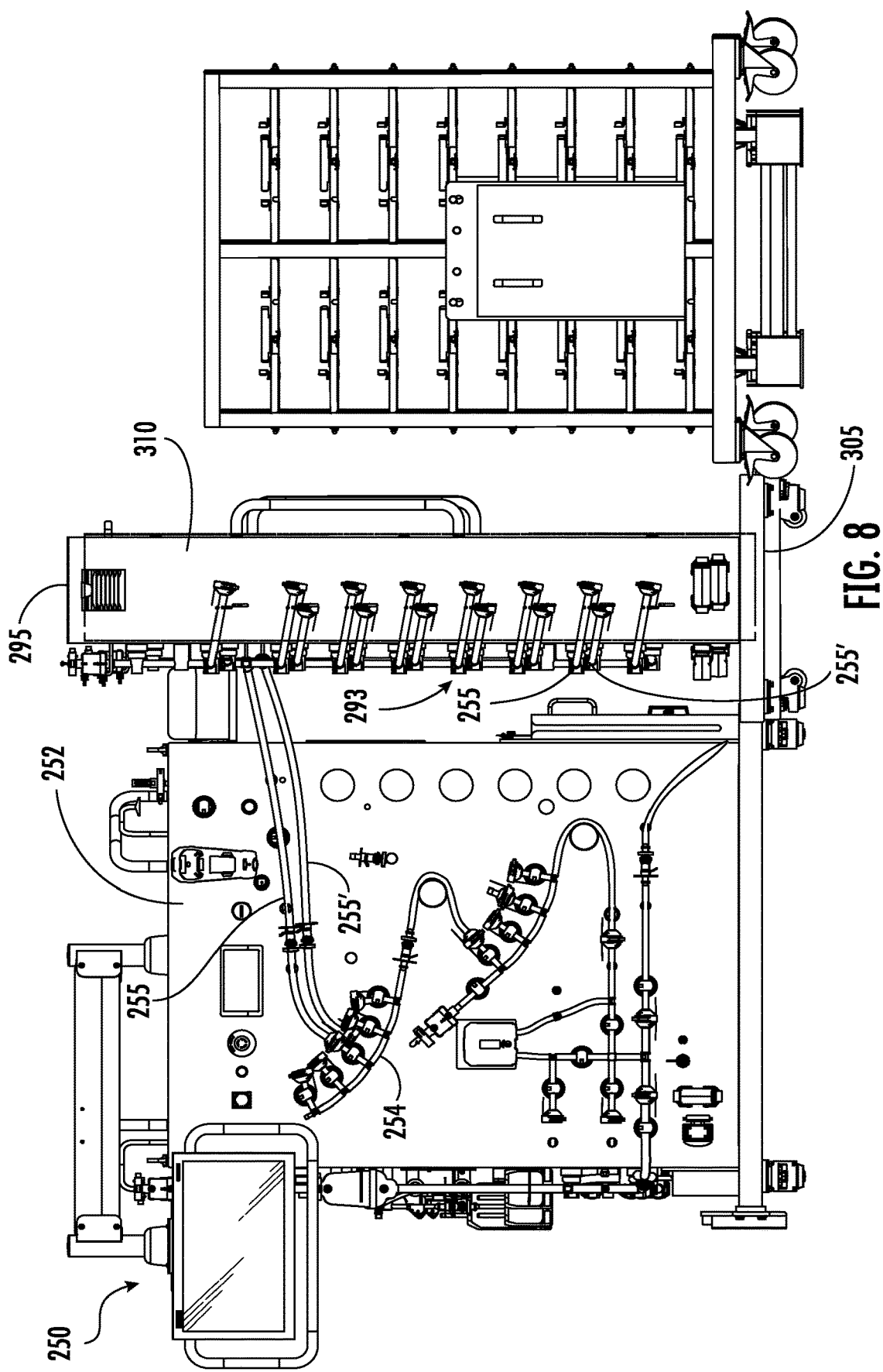
FIG. 8 is an elevational view of the distributor skid, the distribution tower, and the workstation of FIG. 7.

The workstation 100' illustrated in FIGS. 5 and 6 includes a trolley 140, a frame structure 143', and a weigh scale 145. The frame structure 143' is mounted to the trolley 140 and is configured to support one or more biocontainer totes. The frame structure 143' includes an upright structure configured to retain the tote in place and to form a pair of handle portions 152 suitable for gripping when moving the workstation 100' over the surface upon which the wheels of the trolley 140 rest. The workstation 100' comprises a workstation configured to hold fluid in at least one single use tote that the fluid distribution system 50' aliquoted from a larger supply. The workstation 100' of FIG. 5 can be similar in other respects to the workstation 100 of FIG. 3.

Referring to FIGS. 7-10, in embodiments, a fluid distribution system 250 constructed according to principles of the present disclosure includes at least one single use filler manifold 255 and at least one filler valve arrangement 293 mounted to a distribution tower 295 separate from the distributor skid 252. The illustrated distribution tower 295 comprises a trolley 305 and a filling tower 310. The filling tower 310 extends from the trolley 305. In the embodiment shown in FIGS. 7 and 8, two of the set of single use filler manifolds 255, 255' are mounted to the filling tower of the distribution tower. In embodiments, the filler valve arrangement 293 is mounted to the tower 310 and can be associated with one of the single use filler manifolds 255 mounted to the filling tower 310 such that the valves of the filler valve arrangement 293 are respectively associated with each one of the filler manifold outlets. The filler manifold outlets of this single use filler manifold 255 can be placed in respective fluid communication with a corresponding plurality of single use containers that can be supported by the workstations 300, 301.

In embodiments, after the first one of the single use filler manifolds 255 mounted to the filling tower 310 is used in a filling operation, the other of the single use filler manifolds 255' mounted to the filling tower 310 can be associated with the filler valve arrangement 293 mounted to the filling tower 310 and another of the intermediary distributor manifold outlets of the intermediary single use distributor manifold 254. The other of the single use filler manifolds 255' mounted to the filling tower 310 can then be used in a second filling operation with a another set of single use containers.

Figure 9:
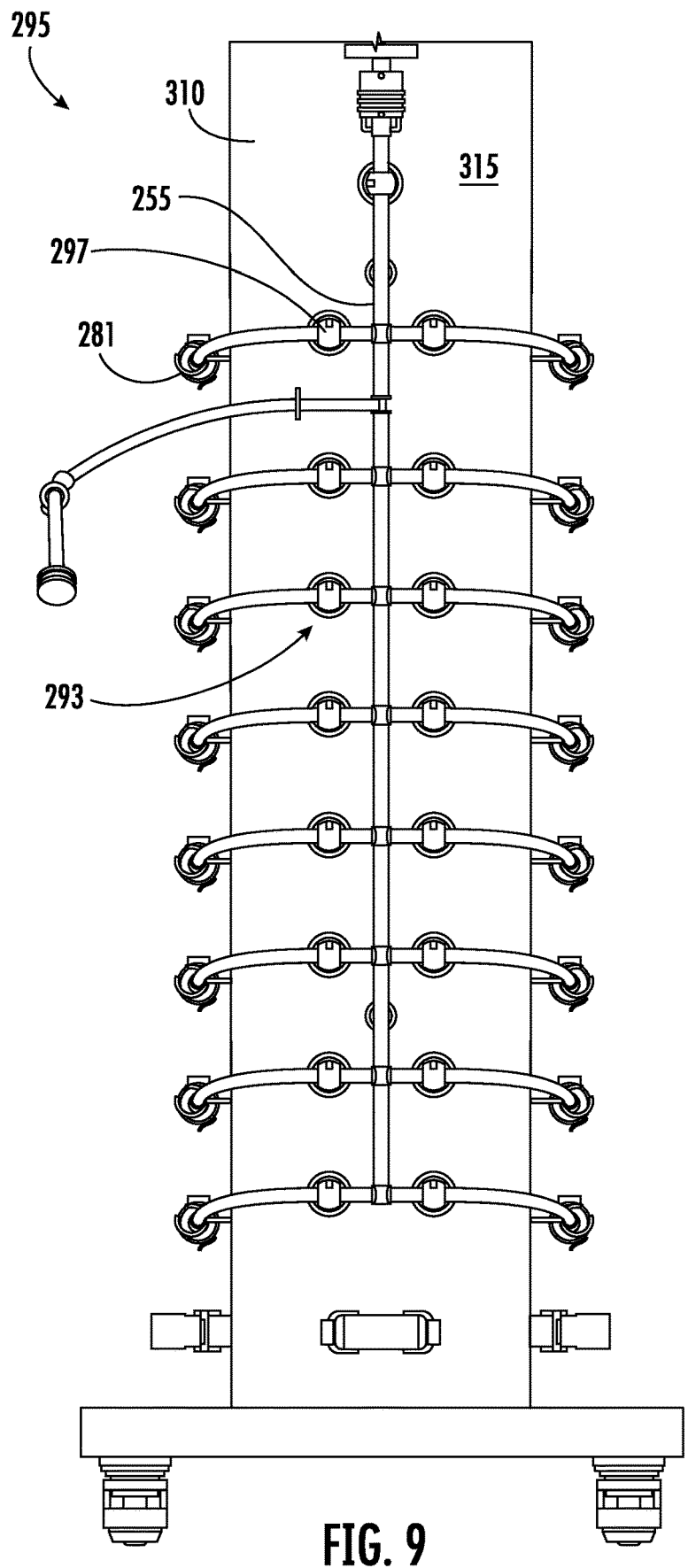
FIG. 9 is another elevational view of the distribution tower of FIG. 7.
Figure 10:
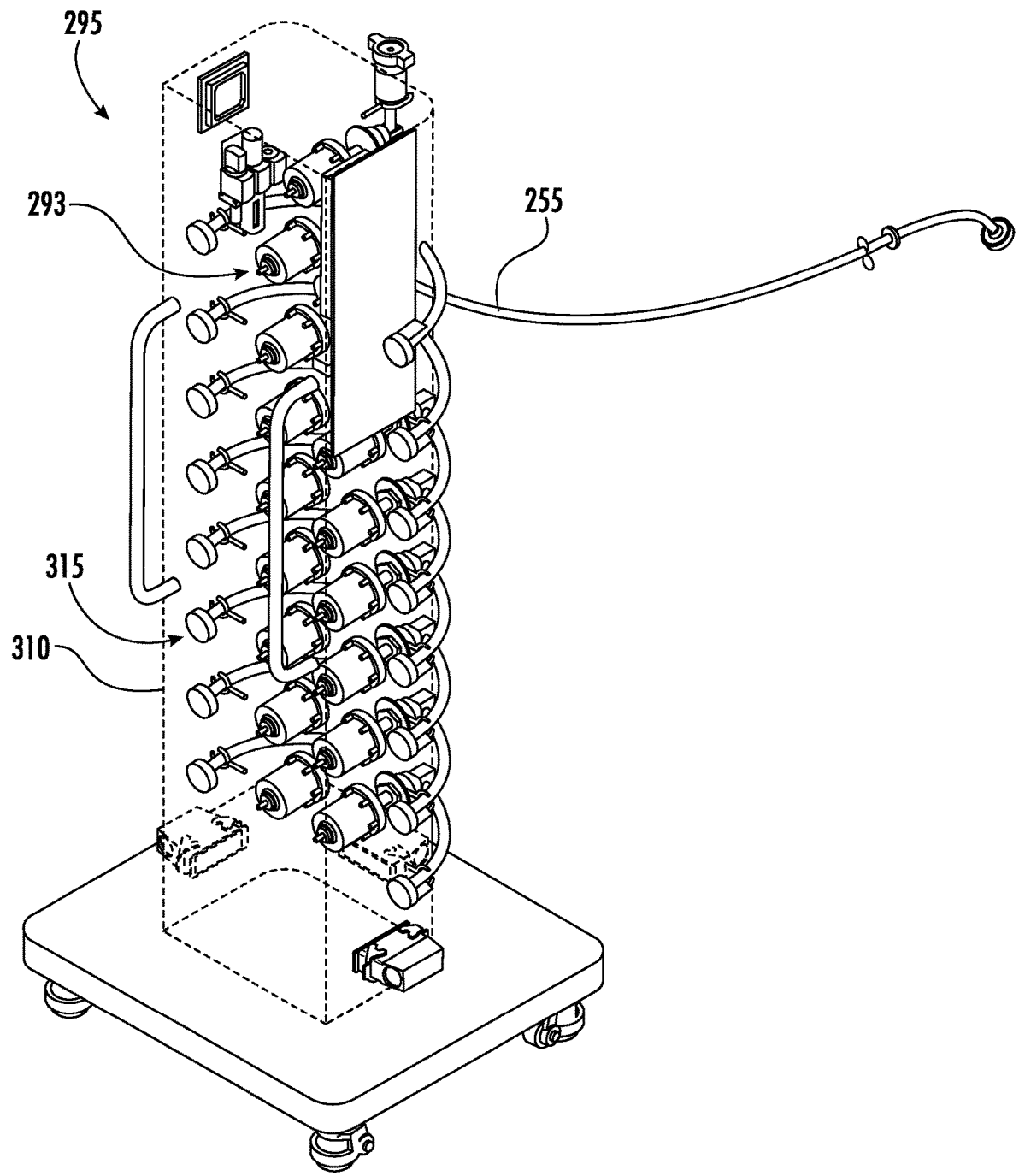
FIG. 10 is a perspective view of the distribution tower of FIG. 7, shown with a cabinet in broken lines for illustrative purposes.

Referring to FIGS. 9 and 10, the filling tower 310 of the distribution tower 295 is shown with a filler valve arrangement 293 and one single use filler manifold 255 mounted thereto. The filling tower 310 includes an enclosure 315 that can support the plurality of valves comprising the filler valve arrangement 293 such that the clamping portions of the valves extends from an exterior surface of the enclosure 315. The clamping portions 297 can be associated with a respective one of the filler manifold outlets 281 as shown in FIG. 9 (only one of which being indicated).

Figure 11:
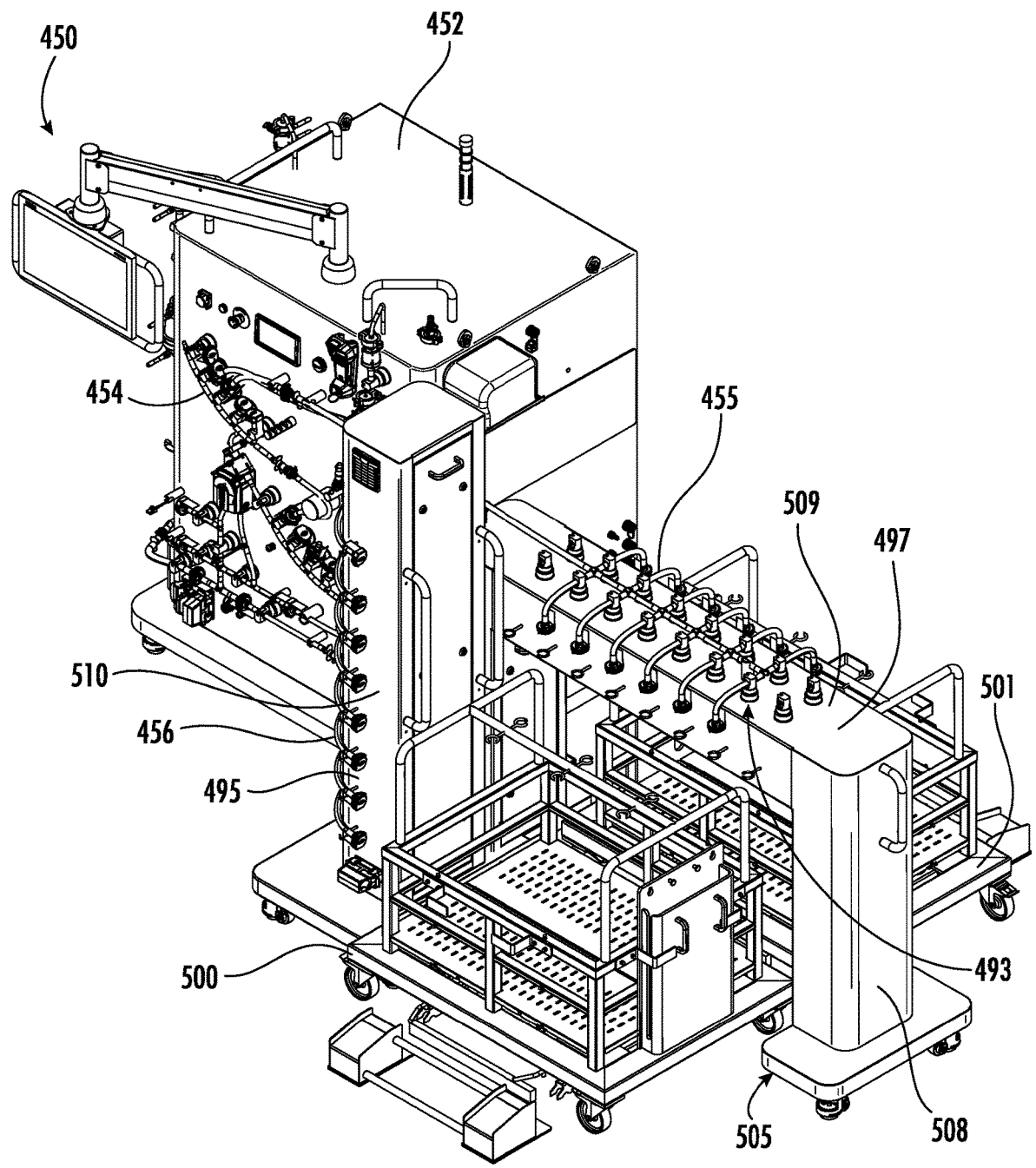
FIG. 11 is a perspective view of another embodiment of a fluid distribution system constructed in accordance with principles of the present disclosure, including a distributor skid, the distribution tower of FIG. 7, and another embodiment of a distribution tower having a single use filler manifold of the fluid distribution system mounted thereto; and a perspective view of another embodiment of a workstation configured to hold a plurality of single use containers for receiving aliquoted portions of fluid from the fluid distribution system.
Figure 12:
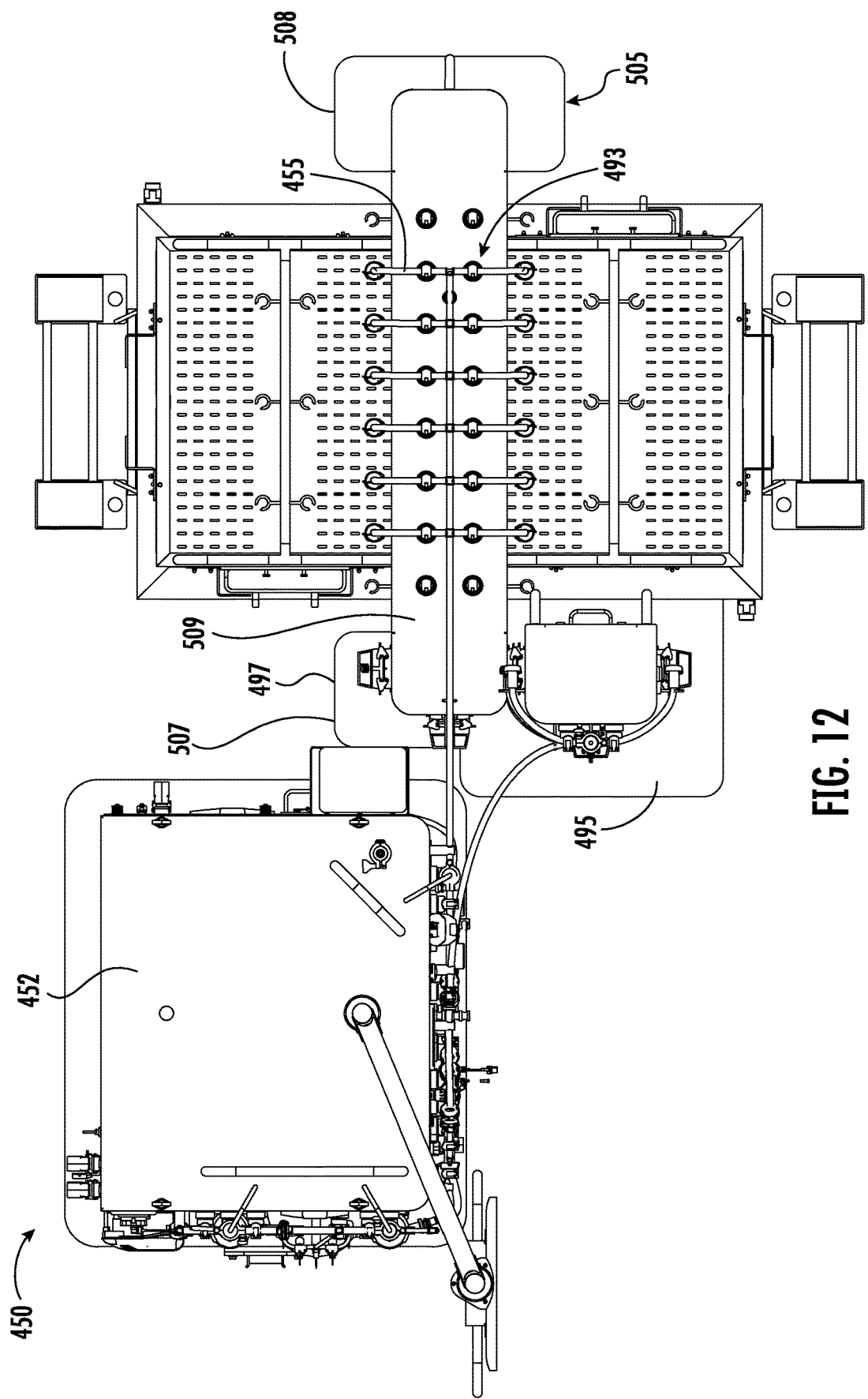
FIG. 12 is a top plan view of the distributor skid, the distribution towers, and the workstation of FIG. 11.

Referring to FIGS. 11 and 12, in embodiments, an embodiment of a fluid distribution system 450 constructed according to principles of the present disclosure includes at least one single use filler manifold 455 and at least one filler valve arrangement 493 mounted to a distribution tower 497 separate from the distributor skid 452. In the embodiment illustrated in FIGS. 11 and 12, a pair of distribution towers 495, 497 are provided. In embodiments, the fluid distribution system 450 includes multiple distribution towers configured to support multiple, different single use containers filled via the fluid distribution system.

In the illustrated embodiment, one distribution tower 495 is similar in construction to the distribution tower 295 of FIGS. 7-10. The other distribution tower 497 comprises a gantry 505 including first and second uprights 507, 508 and a beam 509 extending between upper ends of the first and second uprights 507, 508. Each upright 507, 508 includes a trolley at its base configured to help the mobility of the gantry 505. One of the set of single use filler manifolds 455 and the filler valve arrangement 493 are mounted to the beam.

Referring to FIG. 11, in embodiments, the filler manifold inlet of this single use filler manifold can be placed in fluid communication with one of the intermediary distributor manifold outlets of the single use intermediary distributor manifold 454 mounted to the distributor skid 452. The filler manifold outlets of this single use filler manifold 455 can be placed in respective fluid communication with a corresponding plurality of single use containers that can be supported by the workstations 500, 501.

In embodiments, the filler manifold inlet of the single use filler manifold 456 mounted to the filling tower 510 can be placed in fluid communication with another of the intermediary distributor manifold outlets of the single use intermediary distributor manifold 454 mounted to the distributor skid 452. The filler manifold outlets of this single use filler manifold 456 can be placed in respective fluid communication with another set of single use containers that can be supported by the workstations 500, 501 or other, differently-configured workstations, such as those shown in FIG. 7, for example.

In other embodiments, a fluid distribution system constructed according to principles of the present disclosure can include different equipment configured to hold the supply of fluid for delivery to the manifolds for distributed, scaled dispensing in a plurality of single use containers. For example, in other embodiments, a fluid distribution system constructed according to principles of the present disclosure can include at least one tower configured to hold one or more totes filled with a fluid for use with the fluid distribution system. In other embodiments, a fluid distribution system constructed according to principles of the present disclosure can include one or more tanks filled with a fluid for use in the system.

In other embodiments of a fluid distribution system constructed in accordance with principles of the present disclosure, the fluid distribution system construction can take alternatives forms. For example, in embodiments, the distribution towers can be replaced by totes. In other embodiments, the fluid distribution system can be scaled for larger volumes or decreased for laboratory usage. In embodiments, the fluid distribution system can include single use manifolds constructed from rigid plastic construction. In embodiments, a fluid distribution system constructed according to principles of the present disclosure can be used to process a variety of liquids to meet the requirements of a desired application.

In embodiments of a method of using a fluid distribution system following principles of the present disclosure, a fluid distribution system constructed according to principles of the present disclosure is used to deliver portions of fluid to a series of single use containers as discussed herein. In embodiments, a method of using a fluid distribution system following principles of the present disclosure can be used with any embodiment of a fluid distribution system according to principles discussed herein, which can include an embodiment of a distributor skid having at least one single use distributor manifold according to principles of the present disclosure.

In one embodiment, a method of aseptically distributing fluid includes feeding a fluid into a distributor manifold inlet of a single use distributor manifold. A first supply of the fluid is discharged from a first one of a plurality of distributor manifold outlet ports of the single use distributor manifold to a filler manifold inlet of a first single use filler manifold via a first aseptic fluid pathway. Portions of the first supply of the fluid are respectively discharged from a plurality of filler manifold outlet ports of the first single use filler manifold to a respective one of a first set of single use containers respectively aseptically fluidly connected to the plurality of filler manifold outlet ports of the first single use filler manifold. After the portions of the first supply of the fluid are discharged, the first single use filler manifold is disconnected from the single use distributor manifold.

A second supply of the fluid is discharged from a second one of the plurality of distributor manifold outlet ports of the single use distributor manifold to a filler manifold inlet of a second single use filler manifold via a second aseptic fluid pathway. Portions of the second supply of the fluid are respectively discharged from a plurality of filler manifold outlet ports of the second single use filler manifold to a respective one of a second set of single use containers respectively aseptically fluidly connected to the plurality of filler manifold outlet ports of the second single use filler manifold.

In embodiments, the method further includes sequentially discharging an additional supply of the fluid from each other distributor manifold outlet of the single use distributor manifold to a filler manifold inlet of a respective other single use filler manifold via a respective separate aseptic fluid pathway. Portions of the additional supply of the fluid are respectively discharged from a plurality of filler manifold outlet ports of each respective other single use filler manifold to a respective one of an additional set of single use containers respectively aseptically fluidly connected to the plurality of filler manifold outlet ports of each respective other single use filler manifold. After respectively discharging the portions of the additional supply of the fluid, each respective other single use filler manifold is disconnected from the single use distributor manifold.

In embodiments, the method further includes installing the single use distributor manifold in a filling skid before feeding the fluid into the distributor manifold inlet of the single use distributor manifold. The single use distributor manifold is removed from the filling skid after sequentially discharging the additional supply of the fluid from each other distributor manifold outlet of the single use distributor manifold.

In embodiments, the single use distributor manifold comprises a first single use distributor manifold. In embodiments, the first supply of the fluid is discharged from the first one of a plurality of distributor manifold outlet ports of the single use distributor manifold by feeding the first supply of the fluid into a distributor manifold inlet of a second single use distributor manifold. The second single use distributor manifold in the first aseptic fluid pathway is interposed between the first one of the plurality of distributor manifold outlet ports of the first single use distributor manifold and the filler manifold inlet of the first single use filler manifold, and the first supply of the fluid is discharged from a first one of a plurality of distributor manifold outlet ports of the second single use distributor manifold to the filler manifold inlet of the first single use filler manifold via the first aseptic fluid pathway.

In other embodiments, a method of aseptically distributing fluid includes feeding a first supply of fluid into a distributor manifold inlet of a first single use distributor manifold. A first supply of fluid is discharged from a first one of a plurality of distributor manifold outlet ports of the first single use distributor manifold to a distributor manifold inlet of a second single use distributor manifold via a first aseptic fluid pathway. The first supply of fluid is discharged from a first one of a plurality of distributor manifold outlet ports of the second single use distributor manifold to a filler manifold inlet of a first single use filler manifold via a second aseptic fluid pathway. Portions of the first supply of fluid are respectively discharged from a plurality of filler manifold outlet ports of the first single use filler manifold to a respective one of a first set of single use containers respectively aseptically fluidly connected to the plurality of filler manifold outlet ports of the first single use filler manifold.

After the portions of the first supply of fluid are discharged, the first single use filler manifold is disconnected from the second single use distributor manifold, and a second single use filler manifold is connected to a second one of the plurality of distributor manifold outlet ports of the second single use distributor manifold via a third aseptic fluid pathway. A second supply of fluid is fed into the distributor manifold inlet of the first single use distributor manifold. The second supply of fluid is discharged from the first one of the plurality of distributor manifold outlet ports of the first single use distributor manifold to the distributor manifold inlet of the second single use distributor manifold via the first aseptic fluid pathway. The second supply of fluid is discharged from a second one of the plurality of distributor manifold outlet ports of the second single use distributor manifold to a filler manifold inlet of the second single use filler manifold via the third aseptic fluid pathway. Portions of the second supply of fluid are respectively discharged from a plurality of filler manifold outlet ports of the second single use filler manifold to a respective one of a second set of single use containers respectively aseptically fluidly connected to the plurality of filler manifold outlet ports of the second single use filler manifold.

In embodiments, the method further includes sequentially discharging an additional supply of fluid from each other distributor manifold outlet of the second single use distributor manifold to a filler manifold inlet of a respective other single use filler manifold via a respective separate aseptic fluid pathway. Portions of the additional supply of fluid are respectively discharged from a plurality of filler manifold outlet ports of each respective other single use filler manifold to a respective one of an additional set of single use containers respectively aseptically fluidly connected to the plurality of filler manifold outlet ports of each respective other single use filler manifold.

In embodiments, the method further includes, after respectively discharging the portions of the additional supply of fluid, disconnecting each respective other single use filler manifold from the second single use distributor manifold. In embodiments, the method further includes, after sequentially discharging the additional supply of fluid from each other distributor manifold outlet of the second single use distributor manifold, disconnecting the second single use distributor manifold and connecting a second one of the plurality of distributor manifold outlet ports of the first single use distributor manifold to a distributor manifold inlet of a third single use distributor manifold via a fourth aseptic fluid pathway.

In embodiments, the method further includes feeding a third supply of fluid into the distributor manifold inlet of the first single use distributor manifold. The third supply of fluid is discharged from the second one of the plurality of distributor manifold outlet ports of the first single use distributor manifold to the distributor manifold inlet of the third single use distributor manifold via the fourth aseptic fluid pathway. The third supply of fluid is discharged from a first one of a plurality of distributor manifold outlet ports of the third single use distributor manifold to a filler manifold inlet of a third single use filler manifold via a fifth aseptic fluid pathway. Portions of the third supply of fluid are respectively discharged from a plurality of filler manifold outlet ports of the third single use filler manifold to a respective one of a third set of single use containers respectively aseptically fluidly connected to the plurality of filler manifold outlet ports of the third single use filler manifold.

In embodiments, the method further includes sequentially discharging an additional supply of fluid from each other distributor manifold outlet of the third single use distributor manifold to a filler manifold inlet of a respective other single use filler manifold via a respective separate aseptic fluid pathway. Portions of the additional supply of fluid are respectively discharged from a plurality of filler manifold outlet ports of each respective other single use filler manifold to a respective one of an additional set of single use containers respectively aseptically fluidly connected to the plurality of filler manifold outlet ports of each respective other single use filler manifold.

In embodiments, the method further includes sequentially discharging a respective one of an additional set of supplies of fluid from each other distributor manifold outlet of the first single use distributor manifold to a set of intermediary single use distributor manifolds.

In another embodiment of a method of aseptically distributing fluid following principles of the present disclosure, the method includes sequentially discharging a supply of a fluid from a different one of a plurality of distributor manifold outlet ports of a single use distributor manifold, each of the distributor manifold outlet ports being in fluid communication with a filler manifold inlet of a respective one of a corresponding plurality of single use filler manifolds via a corresponding aseptic fluid conduit, wherein sequentially discharging the supplies of the fluid is performed by operating a valve arrangement to sequence through a series of different conditions including, for each distributor manifold outlet port, the distributor manifold outlet is opened and the other distributor manifold outlet ports are occluded.

In embodiments, for each single use filler manifold, a portion of the supply of the fluid received from the one of the distributor manifold outlet ports in fluid communication therewith is discharged from each of a plurality of filler manifold outlet ports to one of a corresponding set of single use containers respectively aseptically fluidly connected thereto. In embodiments, sequentially discharging the supplies of the fluid is performed by operating a valve arrangement to sequentially open each one of the aseptic fluid conduits with the other aseptic fluid conduits are occluded.

In another embodiment of a method of aseptically distributing fluid following principles of the present disclosure, the method includes feeding a supply of fluid into a filler manifold inlet of a single use filler manifold. A fill portion of the supply of the fluid is discharged respectively from all but a reserved one of a plurality of filler manifold outlets of the first single use filler manifold to single use containers respectively aseptically fluidly connected thereto. After fill portion discharging, an underfill portion of the supply of the fluid is discharged from the reserved one of the filler manifold outlets to a single use container aseptically fluidly connected thereto. The underfill portion is less than the fill portion. After underfill portion discharging, a filler manifold volume of the supply of fluid is drained from a body conduit of the single use filler manifold out of the reserved one of the filler manifold outlets to the single use container aseptically fluidly connected thereto. In embodiments, the underfill portion and the filler manifold volume are together in combination substantially the same as the fill portion.

In embodiments, feeding the supply of fluid into the filler manifold inlet includes priming the body conduit of the single use filler manifold with the filler manifold volume, displacing air in the body conduit out of a vent conduit in fluid communication with the body conduit during priming, and closing the vent conduit after priming. In embodiments, discharging the fill portion comprises sequentially discharging each fill portion. In embodiments, draining the filler manifold volume of the supply of fluid remaining in the body conduit of the single use filler manifold includes opening a vent conduit in fluid communication with the body conduit and replacing the filler manifold volume with air in the body conduit during draining.

In embodiments, the method further includes feeding the supply of fluid into a distributor manifold inlet of a single use distributor manifold. The supply of fluid is discharged from a first one of a plurality of distributor manifold outlets of the single use distributor manifold to the filler manifold inlet of the single use filler manifold via a first aseptic fluid fill pathway. After draining the filler manifold volume of the supply of fluid remaining in the single use filler manifold, the single use containers are disconnected from the single use filler manifold. A distributor manifold volume of the supply of fluid is drained from the single use distributor manifold into an aseptic fluid reserve pathway to a recovery container aseptically fluidly connected thereto. The distributor manifold volume comprises fluid remaining in a body conduit of the single use distributor manifold.

In embodiments, feeding the supply of fluid into the distributor manifold inlet of the single use distributor manifold includes introducing recovery fluid from the recovery container into the distributor manifold inlet via the aseptic fluid reserve pathway such that at least a portion of the supply of fluid comprises recovery fluid from the recovery container. In embodiments, draining the distributor manifold volume of the supply of fluid remaining in the body conduit of the single use distributor manifold includes: (i) opening a vent conduit in fluid communication with the body conduit of the single use distributor manifold, and (ii) opening at least one recovery valve arranged with the first aseptic fluid fill pathway to drain the fluid to a recovery container.

In embodiments, the single use distributor manifold comprises an intermediary single use distributor manifold, and the method further includes feeding the supply of fluid into a distributor manifold inlet of an upstream single use distributor manifold. The supply of fluid is discharged from a first one of a plurality of distributor manifold outlets of the upstream single use distributor manifold to the distributor manifold inlet of the intermediary single use distributor manifold via an aseptic distributor fluid pathway. In embodiments, draining the distributor manifold volume of the supply of fluid includes draining fluid remaining in the single use distributor manifold and the upstream single use distributor manifold. In embodiments, the recovery container is disposed below the single use distributor manifold and the upstream single use distributor manifold in the direction gravity acts upon the distributor manifold volume.

In embodiments, the single use filler manifold comprises a first single use filler manifold, the supply of fluid comprises a first supply of fluid, and the method further includes after fill portion discharging and underfill portion discharging of the first supply of fluid, disconnecting the first single use filler manifold from the single use distributor manifold. In embodiments, the method further includes recovery/draining of any remaining fluid in the filler manifold body to the last outlet port and combining with an underfill portion to make up a full discharge portion before disconnecting the filler manifold.

In embodiments, a filler manifold inlet of a second single use filler manifold is connected to a second one of the plurality of distributor manifold outlets of the single use distributor manifold via a second aseptic fluid fill pathway. A second supply of fluid is fed into the distributor manifold inlet of the single use distributor manifold. In embodiments, feeding the second supply of fluid includes introducing recovery fluid from the recovery container into the distributor manifold inlet via the aseptic fluid reserve pathway such that at least a portion of the second supply of fluid comprises recovery fluid from the recovery container. The second supply of fluid is discharged from the second one of the plurality of distributor manifold outlets of the single use distributor manifold to the filler manifold inlet of the second single use filler manifold via the second aseptic fluid fill pathway. A fill portion of the second supply of fluid is discharged respectively from all but a reserved one of a plurality of filler manifold outlets of the second single use filler manifold to single use containers respectively aseptically fluidly connected thereto. After fill portion discharging, an underfill portion of the second supply of fluid is discharged from the reserved one of the filler manifold outlets of the second single use filler manifold to a single use container aseptically fluidly connected thereto. After underfill portion discharging, a filler manifold volume of the second supply of fluid remaining in a body conduit of the second single use filler manifold is drained out of the reserved one of the filler manifold outlets of the second single use filler manifold to the single use container aseptically fluidly connected thereto.

Referring to FIGS. 13-21, an embodiment of a fluid distribution system 650 constructed in accordance with principles of the present disclosure undergoing a series of fluid recovery sequences is shown. In FIGS. 13-21 the broken line depictions indicate fluid flow paths through the system 650 according to the particular operation being performed.

Figure 14:
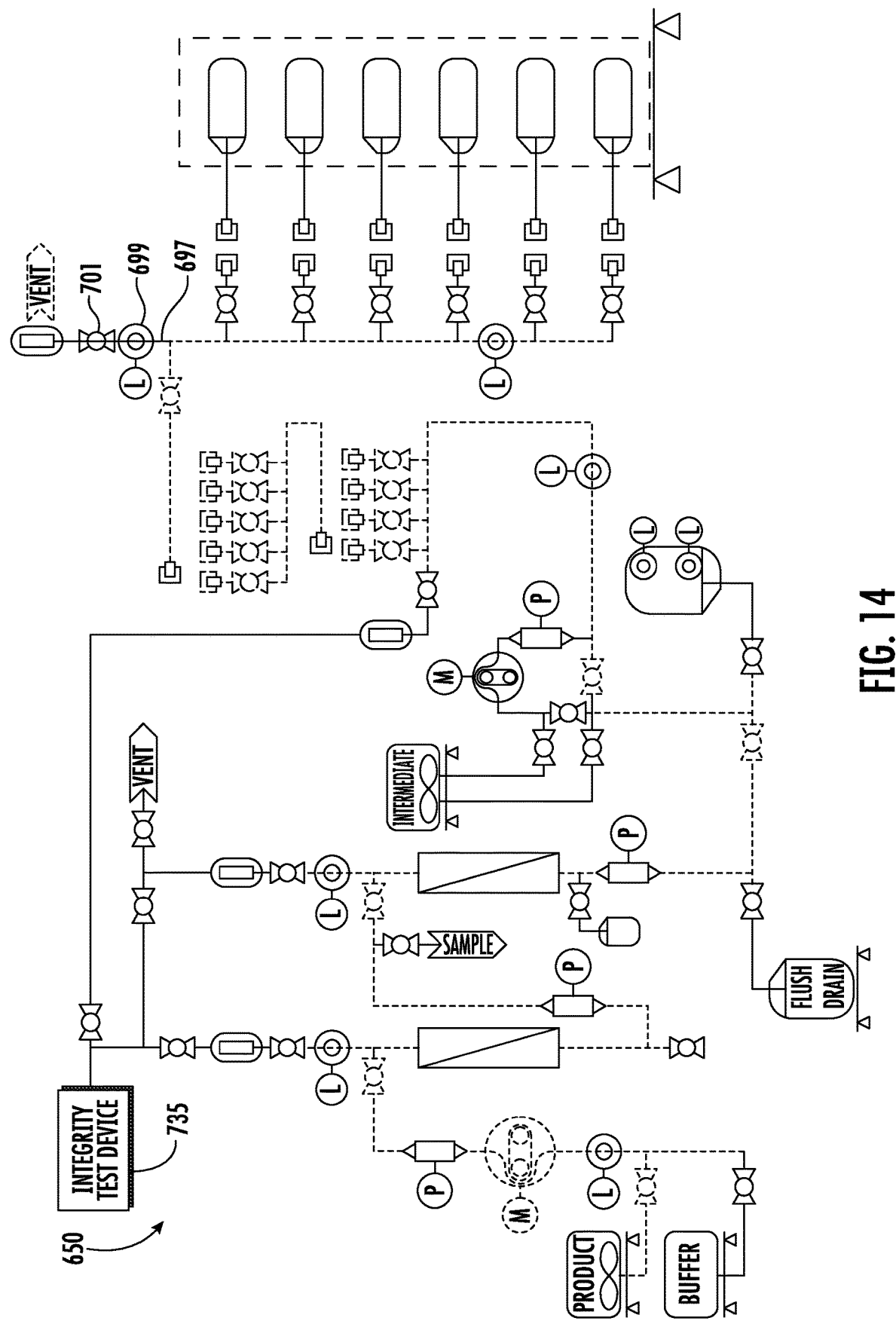
Figure 15:
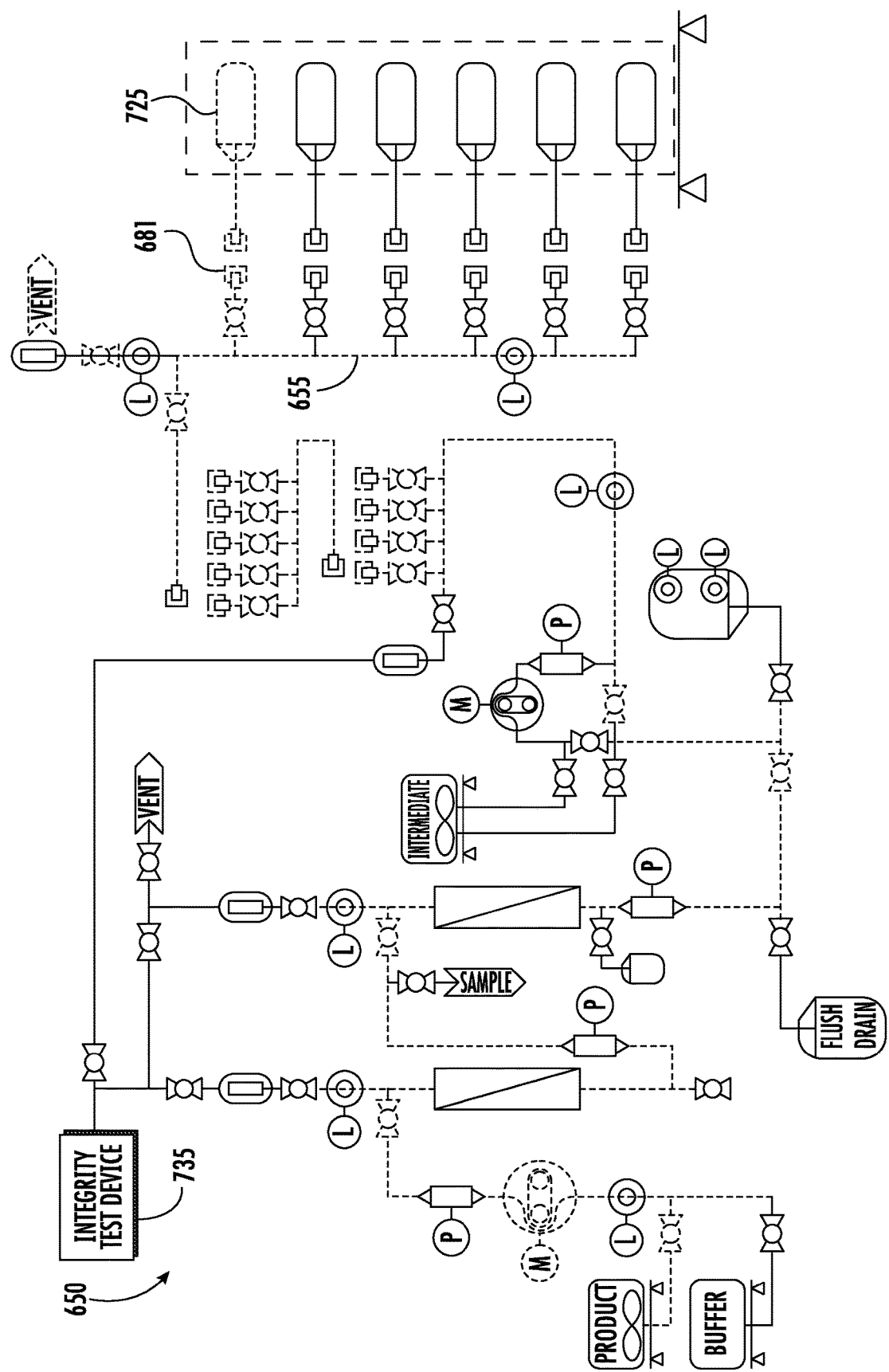
Figure 16:
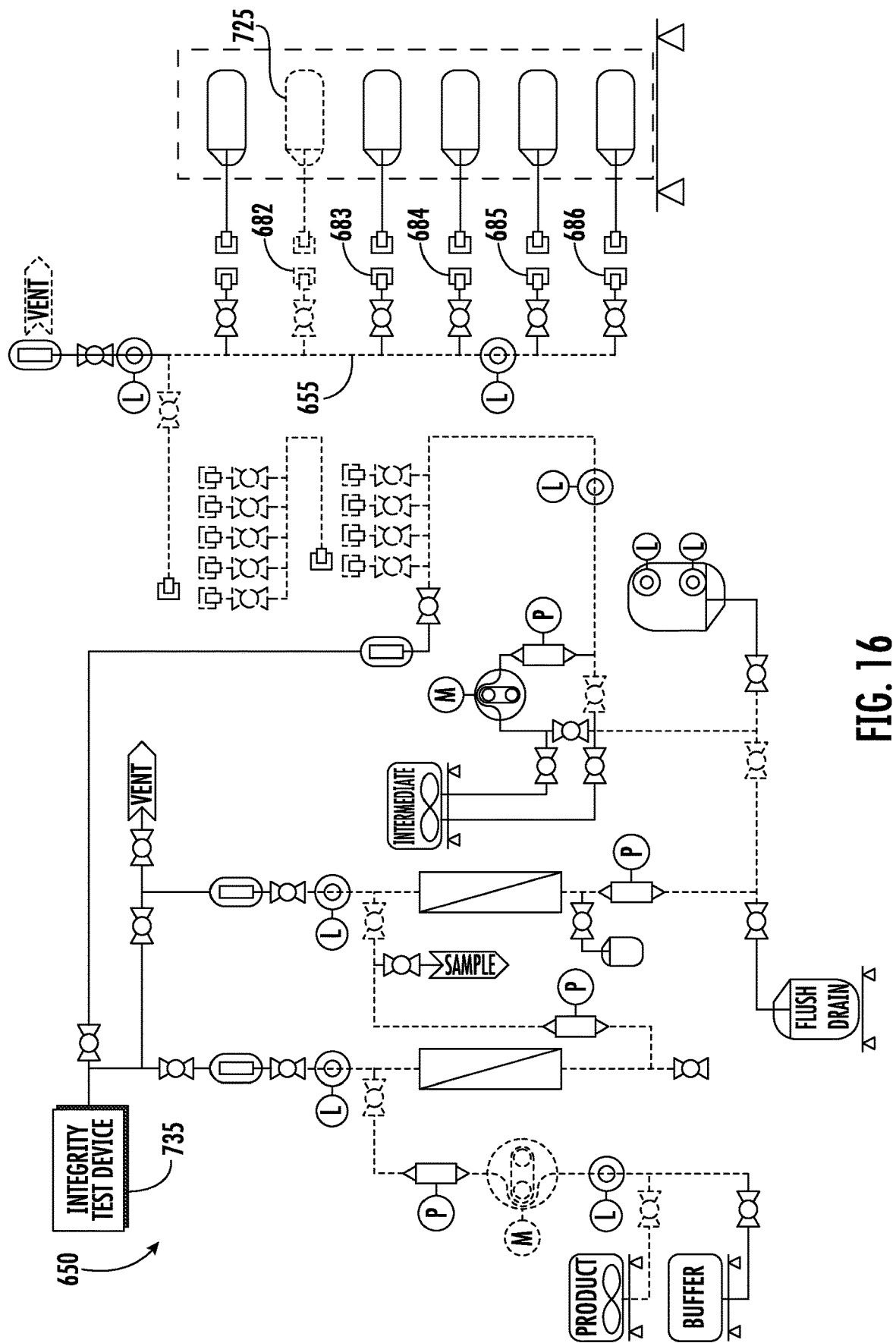
Figure 17:
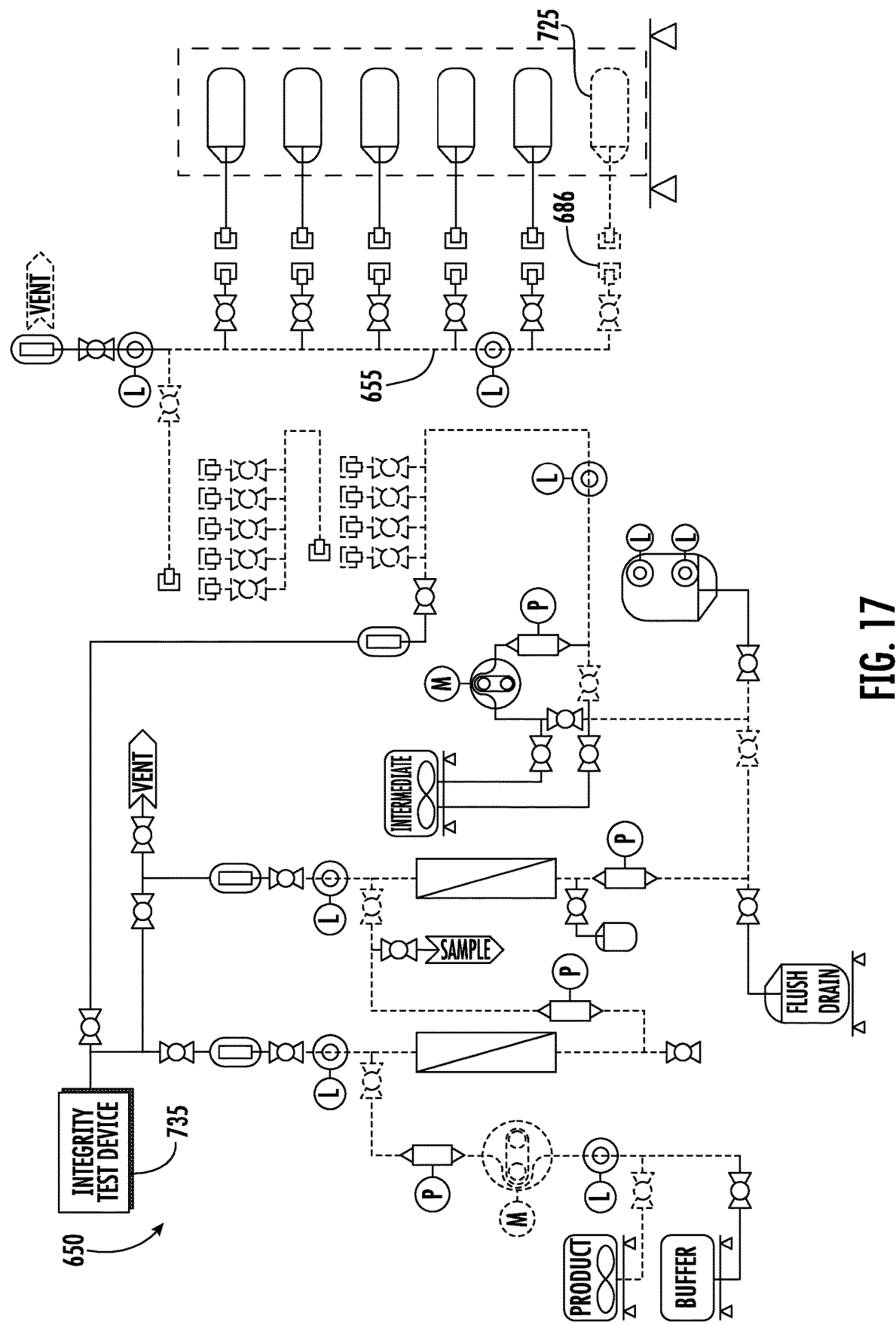
Figure 18:
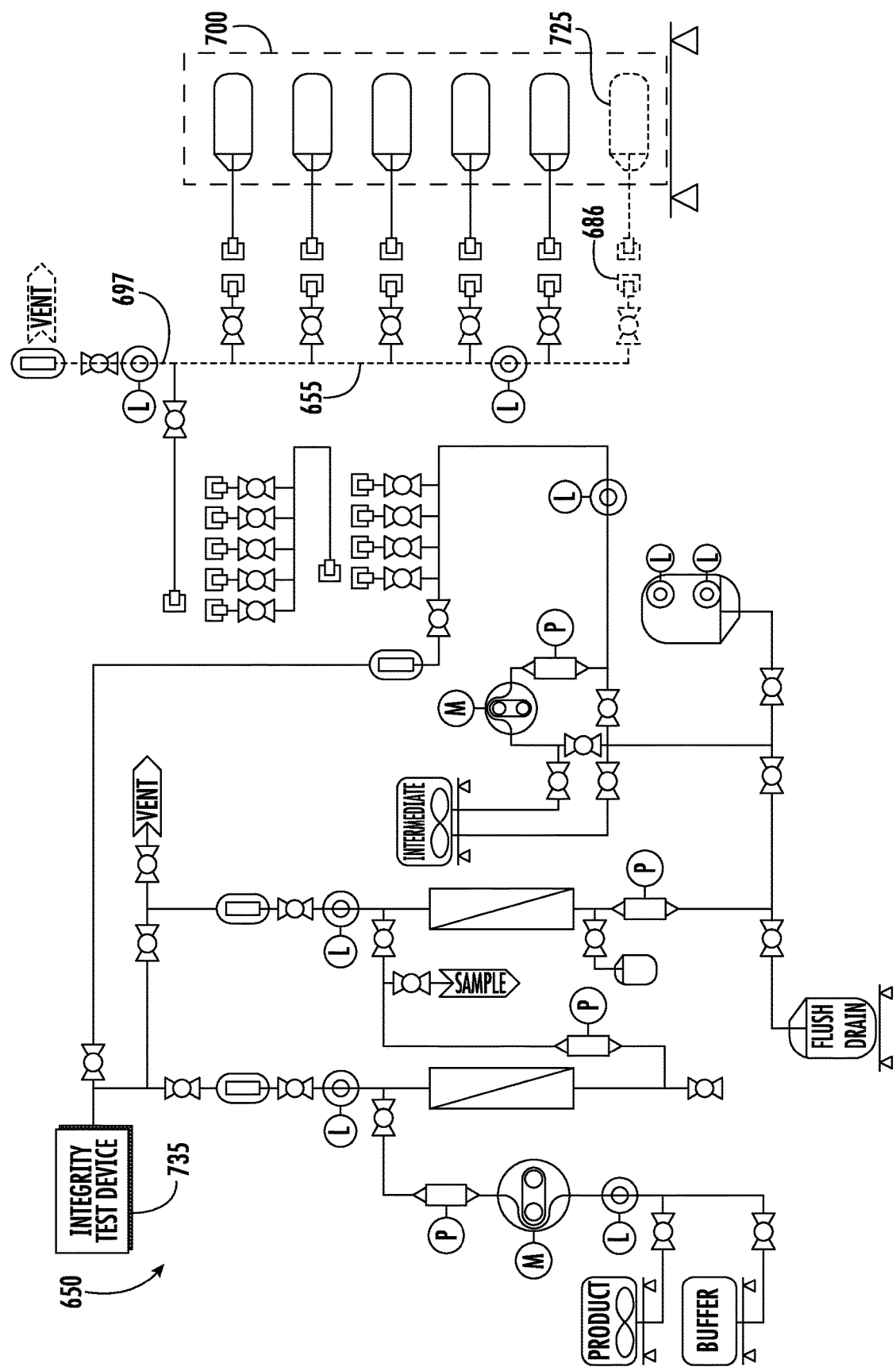

FIGS. 13-18 depict a first fluid recovery sequence in the form of a single use container underfill operation. Referring to FIG. 13, the system 650 can be primed by feeding a supply of fluid 651 from source container(s) to the manifolds 653, 654, 655. The vent conduit 697 above the filler manifold 655 is open so that air is pushed out of the series of manifolds 653-655. In FIG. 14, the vent valve 701 is closed in response to liquid reaching the liquid sensor 699 in the vent conduit 697. FIGS. 15 and 16 show sequential filling through the first and second standard fill outlets 681, 682 of the filler manifold 655 wherein each container 725 connected thereto is filled with the target volume. Referring to FIG. 16, sequential filling can occur in the remainder of the standard fill outlets 683-686. Referring to FIG. 17, an underfill volume is discharged through the underfill outlet 686 of the filler manifold 655 into the single use container 725 in fluid communication therewith. Referring to FIG. 18, the fluid in the filler manifold 655 is drained from the body of the filler manifold out of the underfill outlet 686 into the bottommost container 725 so that each container in the rack 700 contains the target volume. The vent conduit 697 is open during the filler manifold 655 draining operation.

Figure 19:
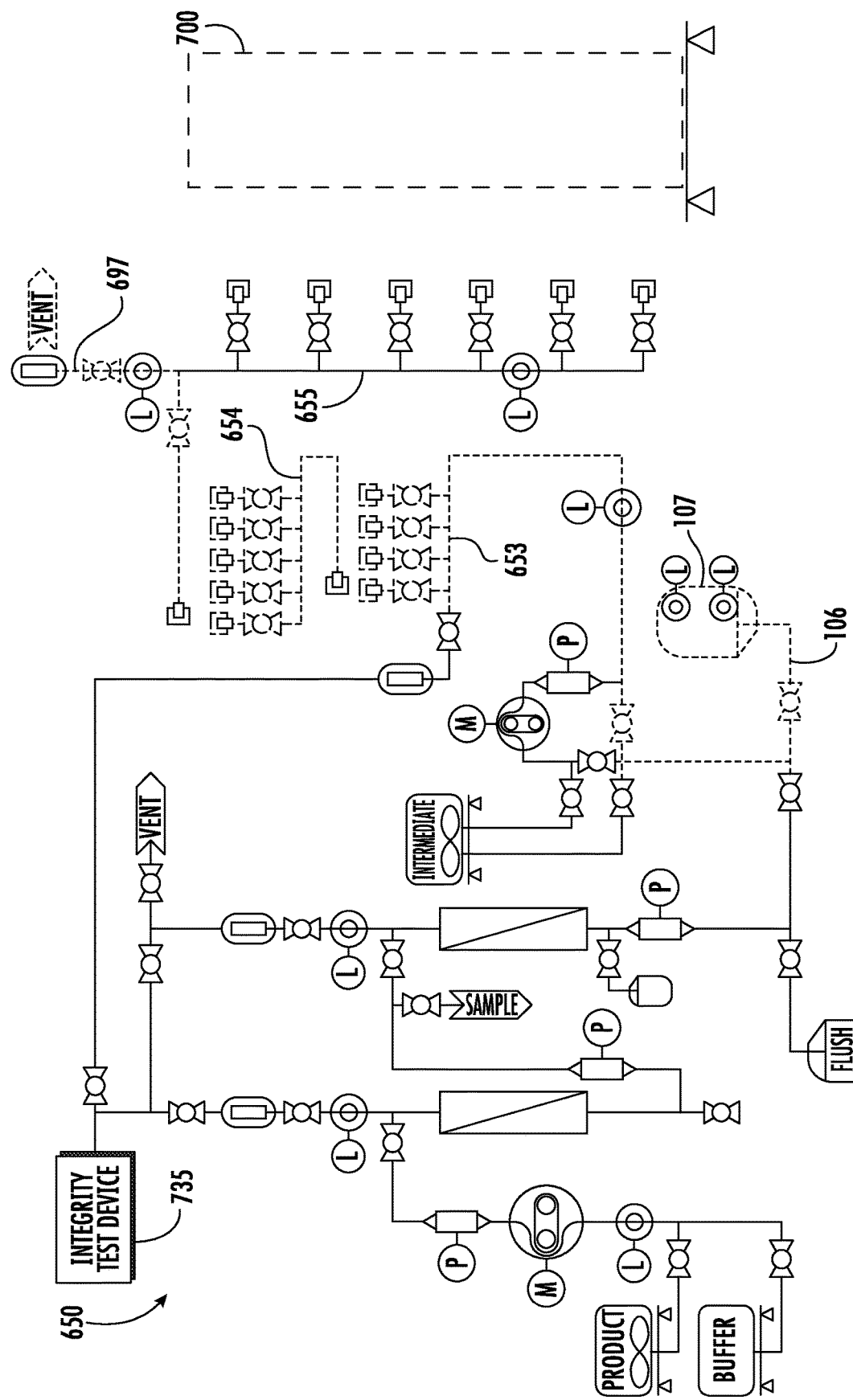
Figure 20:
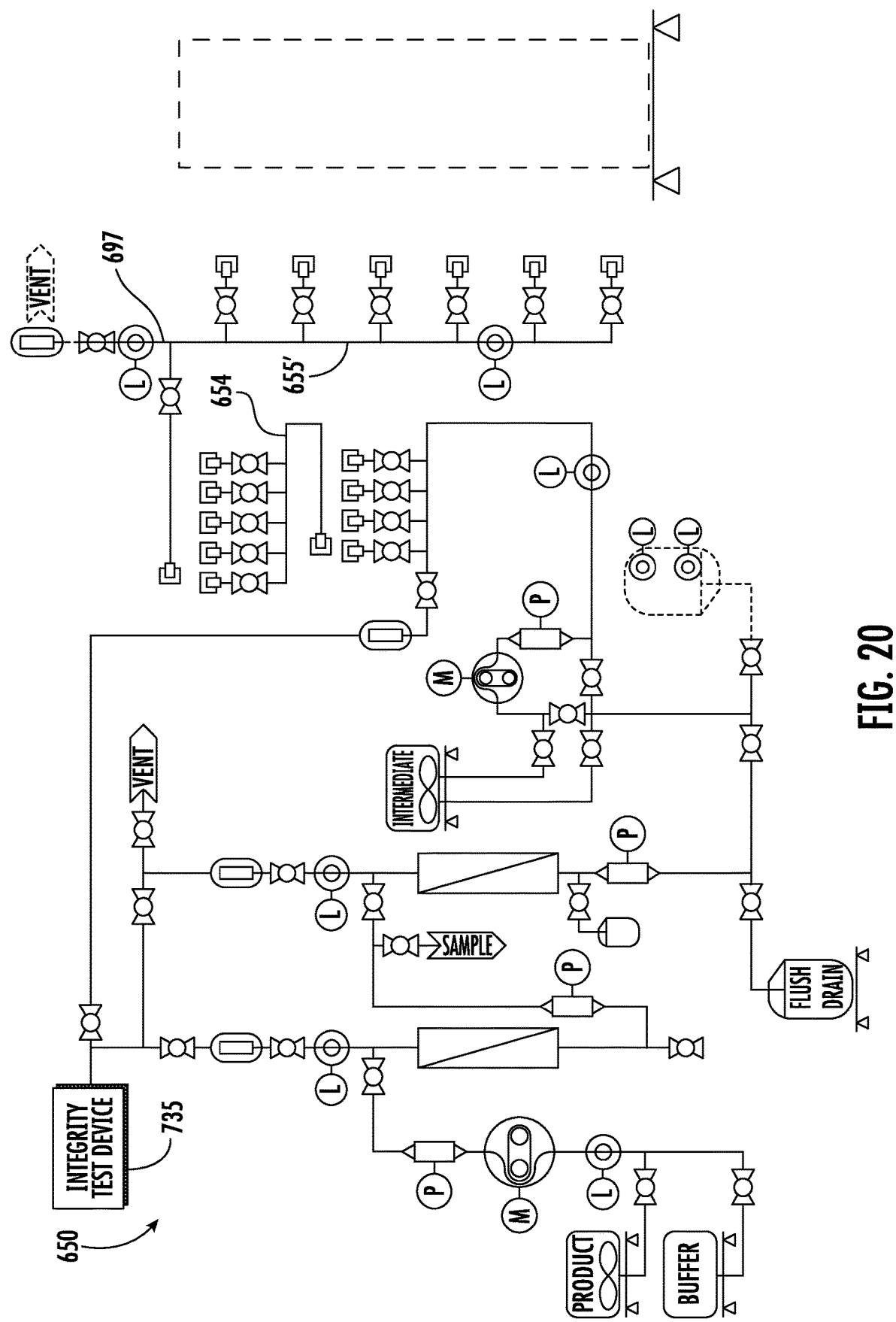

FIGS. 19 and 20 depict a second fluid recovery sequence in the form of a distributor manifold draining operation. Referring to FIG. 19, after filling the single use containers stored in the workstation 700, the containers are disconnected from the filler manifold 655. The vent conduit 697 is opened and the fluid in the distributor manifolds 653, 654 is allowed to drain (via the effect of gravity) to the recovery container 107 by way of the recovery conduit 106. Referring to FIG. 20, once the distributor manifold draining operation is completed, the vent conduit 697 can be closed and a new single use filler manifold 655' can be connected to a different outlet of the intermediary distributor manifold 654.

Figure 21:
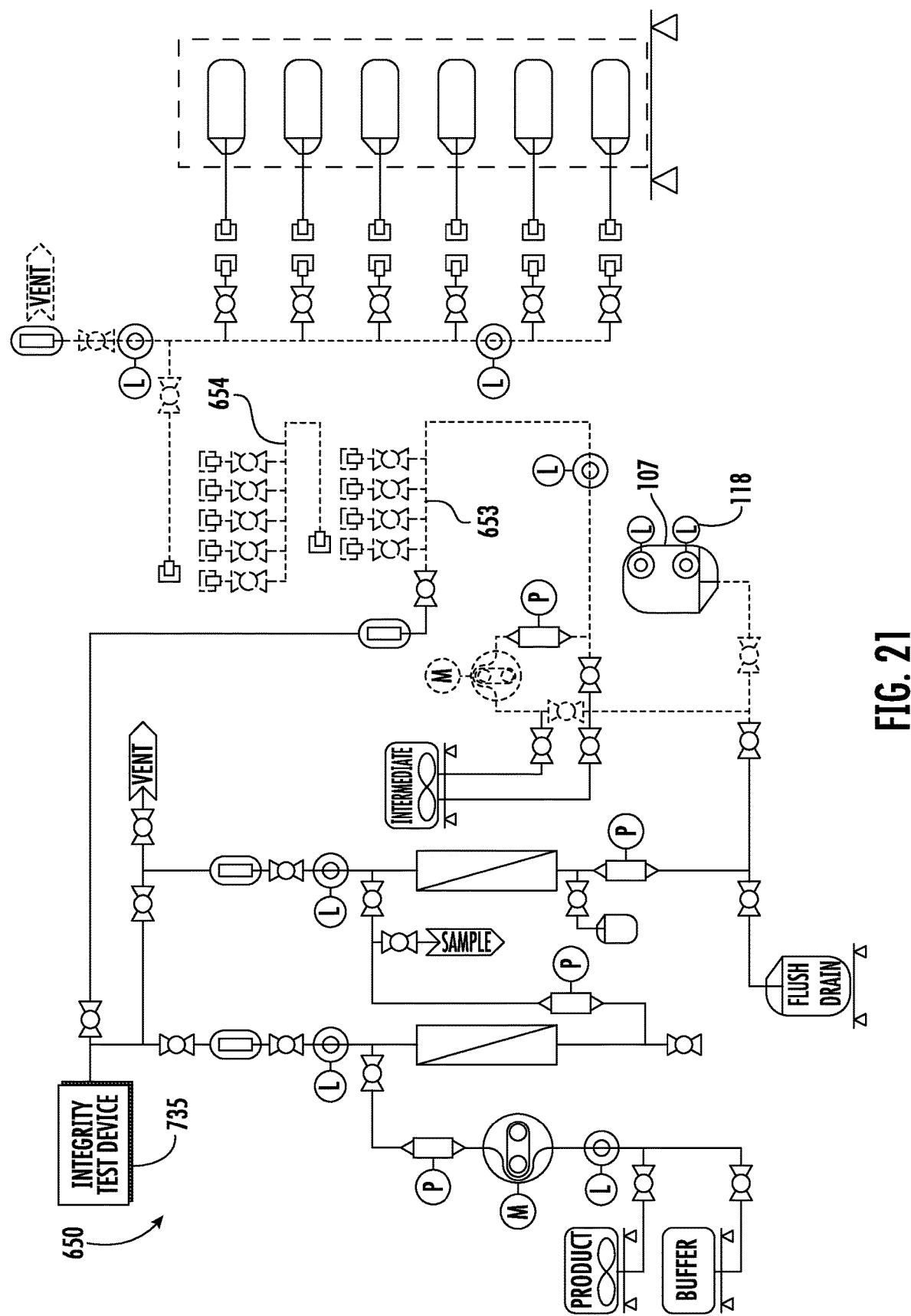

FIG. 21 depicts a third fluid recovery sequence in the form of a manifold priming operation in which fluid from the recovery container 107 is used to prime the manifolds 653, 654. Once the fluid in the recovery container 107 reaches the low level sensor 118, as shown in FIG. 21, the system 650 can deliver a fresh supply of fluid from the original source of fluid 651.

Referring to FIGS. 13-21, in embodiments, the liquid distribution system 650 can include a suitable integrity test device 735 configured to perform an integrity test upon at least one component of the system 650. In embodiments, the integrity test device 735 is configured to conduct an integrity test upon at least one of the manifolds 653-655. A variety of integrity test instruments are suitable for use in accordance with embodiments of the present disclosure, for example, a PALLTRONIC Flowstar IV Filter integrity test instrument, or a PALLTRONIC Flowstar IV Filter integrity test instrument MUX Extension, or a PALLTRONIC Flowstar LGR test instrument, or a PALLTRONIC AquaWIT IV Filter Integrity Test System; Pall Corporation, Port Washington, N.Y. In embodiments, the integrity test device 735 is configured to perform at least one of a leak test and a pressure decay test on at least one of the single use manifolds 653-655.

In embodiments, the fluid distribution system is configured to be used to provide a closed system that can be used for "X" set of filling sequences, wherein the "X" set of filling sequences equals the number of outlets in a first distributor manifold. In embodiments, the fluid distribution system is configured to be used to provide a closed system that can be used for the product of "X" and "Y" sets of filling sequences, wherein the "X" set of filling sequences equals the number of outlets in a first distributor manifold, and the "Y" set of sequences equals the number of outlets in a second distributor manifold connected in series to the first distributor manifold.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A fluid distribution system comprising:
   a pump, the pump adapted to selectively produce a flow of fluid;
   a single use filler manifold, the single use filler manifold including a filler manifold inlet, a plurality of filler manifold outlets, and a filler manifold body conduit, the filler manifold inlet in fluid communication with each one of the plurality of filler manifold outlets via the filler manifold body conduit, the filler manifold inlet arranged with the pump for delivering a supply of fluid to the single use filler manifold, the filler manifold outlets comprising at least one standard fill outlet and an underfill outlet;
   a filler valve arrangement, the filler valve arrangement including a plurality of valves arranged with the single use filler manifold such that each of the filler manifold outlets is independently occludable via a respective one of the valves of the filler valve arrangement;
   a control unit, the control unit including a processor and a non-transitory computer readable medium bearing a fluid distribution program, the processor arranged with the computer readable medium to execute the fluid distribution program, the processor being in electrical communication with the pump and the filler valve arrangement to selectively operate the pump and the valves of the filler valve arrangement based upon instructions from the fluid distribution program, the fluid distribution program having a container filling module configured to discharge a target fill volume of the supply of fluid out of each standard fill outlet of the filler manifold outlets, discharge an underfill volume of the supply of fluid out of the underfill outlet of the filler manifold outlets, and drain a filler manifold volume of the supply of fluid from the filler manifold body conduit out of the underfill outlet of the filler manifold outlets, the underfill volume being less than the target fill volume.

2. The fluid distribution system according to claim 1, further comprising:
a plurality of single use containers, each single use container having an access port fluidly connected to a respective one of the filler manifold outlets via an aseptic fluid connector;
wherein the container filling module of the fluid distribution program is configured to perform the following steps when executed by the processor:
feed the supply of fluid into the filler manifold inlet of the single use filler manifold,
sequentially discharge the target fill volume of fluid respectively from each standard fill outlet of the single use filler manifold into the single use containers respectively aseptically fluidly connected thereto,
after sequential target fill volume discharging, discharge the underfill volume of fluid from the underfill outlet of the single use filler manifold to the single use container aseptically fluidly connected thereto,
after underfill volume discharging, drain the filler manifold volume of fluid from the filler manifold body conduit out of the underfill outlet into the single use container aseptically fluidly connected thereto.

3. The fluid distribution system according to claim 1, further comprising:
a vent conduit, the vent conduit in fluid communication with the filler manifold body conduit;
a vent valve, the vent valve arranged with the vent conduit to selectively occlude the vent conduit, the vent valve in operable arrangement with the control unit.

4. The fluid distribution system according to claim 3, further comprising:
a vent liquid sensor, the vent liquid sensor disposed in the vent conduit, the vent liquid sensor configured to generate a liquid detection signal in response to detecting liquid in the vent conduit, the control unit in electrical communication with the vent liquid sensor to receive the liquid detection signal therefrom;
an air filter, the air filter arranged with the vent conduit, the vent valve interposed between the vent liquid sensor and the air filter;
wherein the control unit is configured to cease operation of the pump and/or close the vent valve in response to receiving the liquid detection signal.

5. The fluid distribution system according to claim 3, wherein the fluid distribution program includes a filler manifold priming module configured to perform the following steps when executed by the processor:
prime the filler manifold body conduit of the single use filler manifold with the filler manifold volume of the supply of fluid,
displace air in the filler manifold body conduit out of the vent conduit during priming the filler manifold body conduit, the vent valve being in an open position, and
place the vent valve in a closed position to occlude the vent conduit after the filler manifold body is primed.

6. The fluid distribution system according to claim 1, further comprising:
a single use distributor manifold, the single use distributor manifold including a distributor manifold inlet, a plurality of distributor manifold outlets, and a distributor manifold body conduit, the distributor manifold inlet in fluid communication with each one of the plurality of distributor manifold outlets via the distributor manifold body conduit, one of the plurality of distributor manifold outlets in aseptic fluid connection with the filler manifold inlet, and the distributor manifold inlet arranged with the pump for delivering the supply of fluid to the single use filler manifold via the one of the distributor manifold outlets;
a distributor valve arrangement, the distributor valve arrangement including a plurality of valves arranged with the single use distributor manifold such that each of the distributor manifold outlets is independently occludable via a respective one of the valves of the distributor valve arrangement.

7. The fluid distribution system according to claim 6, further comprising:
a recovery container and an aseptic fluid reserve pathway, the recovery container in fluid communication with the distributor manifold body conduit via the aseptic fluid reserve pathway;
wherein the fluid distribution program includes a distributor manifold draining module configured, when executed by the processor, to drain a distributor manifold volume of the supply of fluid in the distributor manifold body conduit into the aseptic fluid reserve pathway to the recovery container.

8. The fluid distribution system according to claim 7, further comprising:
a vent conduit, the vent conduit in fluid communication with the filler manifold body conduit;
a vent valve, the vent valve arranged with the vent conduit to selectively occlude the vent conduit, the vent valve in operable arrangement with the control unit;
a recovery valve, the recovery valve arranged with the aseptic fluid reserve pathway such that the aseptic fluid reserve pathway is occludable via the recovery valve, the recovery valve in operable arrangement with the control unit;
wherein the recovery container is disposed below, in the direction gravity acts upon the distributor manifold volume, the vent valve and the single use distributor manifold;
wherein the distributor manifold draining module is configured, when executed by the processor, to open the vent valve to admit air from outside the vent conduit into the distributor manifold body conduit, and to open the recovery valve arranged with the first aseptic fluid fill pathway.

9. The fluid distribution system according to claim 8, further comprising:
a recovery high liquid sensor, the recovery high liquid sensor arranged with the recovery container and configured to generate a high recovery liquid level signal in response to detecting liquid in the recovery container at a predetermined high level, the control unit in electrical communication with the high recovery liquid sensor to receive the high recovery liquid level signal therefrom;
wherein the distributor manifold draining module is configured, when executed by the processor, in response to receiving the high recovery liquid level signal, to close the vent valve, and to close the recovery valve arranged with the first aseptic fluid fill pathway.

10. The fluid distribution system according to claim 6, wherein the single use distributor manifold comprises an intermediary single use distributor manifold, the system further comprising:
an upstream single use distributor manifold, the upstream single use distributor manifold including an upstream distributor manifold inlet, a plurality of upstream distributor manifold outlets, and an upstream distributor manifold body conduit, the upstream distributor manifold inlet in fluid communication with each one of the plurality of upstream distributor manifold outlets via the upstream distributor manifold body conduit, one of the plurality of upstream distributor manifold outlets in aseptic fluid connection with the distributor manifold inlet of the intermediary single use distributor manifold, and the upstream distributor manifold inlet arranged with the pump for delivering the supply of fluid to the single use filler manifold;
an upstream distributor valve arrangement, the upstream distributor valve arrangement including a plurality of valves arranged with the upstream single use distributor manifold such that each of the upstream distributor manifold outlets is independently occludable via a respective one of the valves of the upstream distributor valve arrangement.

11. A method of aseptically distributing fluid, the method comprising:
feeding a supply of fluid into a filler manifold inlet of a single use filler manifold;
discharging a fill portion of the supply of fluid respectively from all but a reserved one of a plurality of filler manifold outlets of the single use filler manifold to single use containers respectively aseptically fluidly connected thereto;
after fill portion discharging, discharging an underfill portion of the supply of fluid from the reserved one of the filler manifold outlets to a single use container aseptically fluidly connected thereto, the underfill portion being less than the fill portion;
after underfill portion discharging, draining a filler manifold volume of the supply of fluid from a body conduit of the single use filler manifold out of the reserved one of the filler manifold outlets to the single use container aseptically fluidly connected thereto.

12. The method according to claim 11, wherein draining the filler manifold volume of the supply of fluid remaining in the body conduit of the single use filler manifold includes opening a manifold vent in fluid communication with the body conduit and replacing the filler manifold volume with air in the body conduit during draining.

13. The method according to claim 12, wherein feeding the supply of fluid into the filler manifold inlet includes priming the body conduit of the single use filler manifold with the filler manifold volume, displacing air in the body conduit out of the manifold vent in fluid communication with the body conduit during priming, and closing the manifold vent after priming.

14. The method according to claim 11, wherein discharging the fill portion comprises sequentially discharging each fill portion.

15. The method according to claim 11, wherein the underfill portion and the filler manifold volume are together in combination substantially the same as the fill portion.

16. The method according to claim 11, further comprising:
feeding the supply of fluid into a distributor manifold inlet of a single use distributor manifold;
discharging the supply of fluid from a first one of a plurality of distributor manifold outlets of the single use distributor manifold to the filler manifold inlet of the single use filler manifold via a first aseptic fluid fill pathway;
after draining the filler manifold volume of the supply of fluid remaining in the single use filler manifold, disconnecting the single use containers from the single use filler manifold;
draining a distributor manifold volume of the supply of fluid from the single use distributor manifold into an aseptic fluid reserve pathway to a recovery container aseptically fluidly connected thereto.

17. The method according to claim 16, wherein feeding the supply of fluid into the distributor manifold inlet of the single use distributor manifold includes introducing recovery fluid from the recovery container into the distributor manifold inlet via the aseptic fluid reserve pathway such that at least a portion of the supply of fluid comprises recovery fluid from the recovery container.

18. The method according to claim 16, wherein draining the distributor manifold volume of the supply of fluid remaining in the body conduit of the single use distributor manifold includes opening a manifold vent in fluid communication with the body conduit of the single use distributor manifold, and opening at least one recovery valve arranged with the first aseptic fluid fill pathway.

19. The method according to claim 16, wherein the single use distributor manifold comprises an intermediary single use distributor manifold, and the method further comprising:
feeding the supply of fluid into a distributor manifold inlet of an upstream single use distributor manifold;
discharging the supply of fluid from a first one of a plurality of distributor manifold outlets of the upstream single use distributor manifold to the distributor manifold inlet of the intermediary single use distributor manifold via an aseptic distributor fluid pathway;
wherein draining the distributor manifold volume of the supply of fluid includes draining fluid remaining in the single use distributor manifold and the upstream single use distributor manifold, and wherein the recovery container is disposed below the single use distributor manifold and the upstream single use distributor manifold in the direction gravity acts upon the distributor manifold volume.

20. The method according to claim 16, wherein the single use filler manifold comprises a first single use filler manifold, and the supply of fluid comprises a first supply of fluid, the method further comprising:
after fill portion discharging and underfill portion discharging of the first supply of fluid, disconnecting the first single use filler manifold from the single use distributor manifold;
connecting a filler manifold inlet of a second single use filler manifold to a second one of the plurality of distributor manifold outlets of the single use distributor manifold via a second aseptic fluid fill pathway;
feeding a second supply of fluid into the distributor manifold inlet of the single use distributor manifold, wherein feeding the second supply of fluid includes introducing recovery fluid from the recovery container into the distributor manifold inlet via the aseptic fluid reserve pathway such that at least a portion of the second supply of fluid comprises recovery fluid from the recovery container;

discharging the second supply of the fluid from the second one of the plurality of distributor manifold outlets of the single use distributor manifold to the filler manifold inlet of the second single use filler manifold via the second aseptic fluid fill pathway;

discharging a fill portion of the second supply of fluid respectively from all but a reserved one of a plurality of filler manifold outlets of the second single use filler manifold to single use containers respectively aseptically fluidly connected thereto;

after fill portion discharging, discharging an underfill portion of the second supply of fluid from the reserved one of the filler manifold outlets of the second single use filler manifold to a single use container aseptically fluidly connected thereto;

after underfill portion discharging, draining a filler manifold volume of the second supply of fluid remaining in a body conduit of the second single use filler manifold out of the reserved one of the filler manifold outlets of the second single use filler manifold to the single use container aseptically fluidly connected thereto.

\* \* \* \* \*